(12) United States Patent
Ashraf et al.

(10) Patent No.: US 12,303,360 B2
(45) Date of Patent: May 20, 2025

(54) NONWOVEN WEBS WITH VISUALLY DISCERNIBLE PATTERNS AND IMPROVED TEXTURE PERCEPTION

(71) Applicant: The Procter & Gamble Company, Cincinnati, OH (US)

(72) Inventors: Arman Ashraf, Mason, OH (US); Aniruddha Chatterjee, Kelkheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 1199 days.

(21) Appl. No.: 17/113,245

(22) Filed: Dec. 7, 2020

(65) Prior Publication Data
US 2021/0169710 A1 Jun. 10, 2021

Related U.S. Application Data

(60) Provisional application No. 62/946,047, filed on Dec. 10, 2019.

(51) Int. Cl.
A61F 13/15 (2006.01)
A61F 13/511 (2006.01)
A61F 13/513 (2006.01)
A61F 13/514 (2006.01)
A61F 13/534 (2006.01)
(Continued)

(52) U.S. Cl.
CPC ...... A61F 13/15203 (2013.01); A61F 13/511 (2013.01); A61F 13/51104 (2013.01);
(Continued)

(58) Field of Classification Search
None
See application file for complete search history.

(56) References Cited

U.S. PATENT DOCUMENTS 4,333,979 A 6/1982 Sciaraffa
4,514,345 A 4/1985 Johnson et al.
(Continued)

FOREIGN PATENT DOCUMENTS

CN 1209177 A 2/1999
CN 1441102 A 9/2003
(Continued)

OTHER PUBLICATIONS

Machine Translation of JPH0318546Y2 (Published Patent of Application JP 61111993 U), Apr. 1991 (Year: 1991).*
(Continued)

Primary Examiner — Jeffrey A Vonch
(74) Attorney, Agent, or Firm — Christian M. Best

(57) ABSTRACT

A nonwoven web for an absorbent article is provided. The nonwoven web comprises a first surface, a second surface, and a visually discernible pattern of three-dimensional features on the first surface or the second surface. The three-dimensional features comprise one or more first regions and a plurality of second regions. The one or more first regions have a first value of an average intensive property. The plurality second regions have a second value of the average intensive property. The first value and the second value are different and are both greater than zero. The nonwoven web has a Single Layer Chroma value in the range of about 1.0 to about 3.5, according to the Delta Chroma and Single Layer Chroma Test. The nonwoven web has a Delta Chroma value in the range of about +0.1 to about +3.5, according to the Delta Chroma and Single Layer Chroma Test.

22 Claims, 19 Drawing Sheets

(51) Int. Cl.
*B32B 5/02* (2006.01)
*B32B 33/00* (2006.01)
*D04H 3/018* (2012.01)
*D04H 3/14* (2012.01)

(52) U.S. Cl.
CPC .. *A61F 13/51113* (2013.01); *A61F 13/51394* (2013.01); *A61F 13/51462* (2013.01); *A61F 13/51476* (2013.01); *A61F 13/51496* (2013.01); *A61F 13/534* (2013.01); *B32B 5/022* (2013.01); *B32B 33/00* (2013.01); *A61F 2013/15243* (2013.01); *A61F 2013/15284* (2013.01); *A61F 2013/15373* (2013.01); *A61F 2013/15406* (2013.01); *A61F 2013/15422* (2013.01); *B32B 2307/40* (2013.01); *B32B 2307/4026* (2013.01); *B32B 2555/02* (2013.01); *D04H 3/018* (2013.01); *D04H 3/14* (2013.01); *Y10T 428/24479* (2015.01); *Y10T 428/24603* (2015.01); *Y10T 428/24612* (2015.01); *Y10T 428/31* (2015.01); *Y10T 442/60* (2015.04); *Y10T 442/681* (2015.04)

(56) References Cited

U.S. PATENT DOCUMENTS

| | | | |
|---|---|---|---|
| 4,741,941 A | 5/1988 | Englebert | |
| 4,789,699 A | 12/1988 | Kieffer et al. | |
| 4,970,104 A | 11/1990 | Radwanski | |
| 5,131,910 A * | 7/1992 | Breault | D21H 21/28 8/919 |
| 5,145,727 A | 9/1992 | Potts et al. | |
| 5,178,932 A * | 1/1993 | Perkins | B32B 27/34 428/447 |
| 5,302,220 A | 4/1994 | Terakawa et al. | |
| 5,334,289 A | 8/1994 | Trokhan | |
| 5,368,858 A | 11/1994 | Hunziker | |
| 5,369,858 A | 12/1994 | Gilmore et al. | |
| 5,514,523 A | 5/1996 | Trokhan | |
| 5,575,874 A | 11/1996 | Griesbach, III | |
| 5,599,420 A | 2/1997 | Yeo | |
| 5,634,653 A | 6/1997 | Browning | |
| 5,643,653 A | 7/1997 | Griesbach, III | |
| 5,725,927 A | 3/1998 | Zilg et al. | |
| 5,814,178 A * | 9/1998 | Jacobs | B29C 61/02 156/290 |
| 5,821,178 A * | 10/1998 | Cohen | B32B 27/12 442/389 |
| 5,834,384 A * | 11/1998 | Cohen | D04H 1/4291 427/538 |
| 5,858,504 A | 1/1999 | Fitting | |
| 5,895,623 A | 4/1999 | Trokhan | |
| 5,916,661 A | 6/1999 | Benson | |
| 6,087,551 A * | 7/2000 | Pereira | A61F 13/51121 604/385.01 |
| 6,139,941 A | 10/2000 | Jankevics | |
| 6,319,455 B1 | 11/2001 | Kauschke et al. | |
| 6,331,268 B1 | 12/2001 | Kauschke et al. | |
| 6,331,345 B1 | 12/2001 | Kauschke et al. | |
| 6,361,638 B2 | 3/2002 | Takai | |
| 6,383,431 B1 | 5/2002 | Dobrin | |
| 6,395,957 B1 | 5/2002 | Chen | |
| 6,436,512 B1 | 8/2002 | Kauschke et al. | |
| 6,632,504 B1 | 10/2003 | Gillespie | |
| 6,673,418 B1 | 1/2004 | Deolivera | |
| 6,818,802 B2 | 11/2004 | Takai et al. | |
| 6,841,037 B2 | 1/2005 | Scherb et al. | |
| 6,888,046 B2 | 5/2005 | Toyoshima et al. | |
| 7,005,044 B2 | 2/2006 | Kramer et al. | |
| 7,168,473 B2 | 1/2007 | Geus et al. | |
| 7,255,759 B2 | 8/2007 | Debyser et al. | |
| 7,507,463 B2 | 3/2009 | Noda et al. | |
| 7,553,535 B2 | 6/2009 | Noda et al. | |
| 7,578,317 B2 | 8/2009 | Levine et al. | |
| 7,662,462 B2 | 2/2010 | Noda et al. | |
| 7,897,240 B2 | 3/2011 | Noda et al. | |
| 7,954,213 B2 | 6/2011 | Mizutani | |
| 7,955,549 B2 | 6/2011 | Noda et al. | |
| 8,129,298 B2 | 3/2012 | Motomura | |
| 8,143,177 B2 | 3/2012 | Noda | |
| 8,183,431 B2 | 5/2012 | Noda et al. | |
| 8,273,941 B2 | 9/2012 | Uematsu et al. | |
| 8,304,600 B2 | 11/2012 | Noda et al. | |
| 8,574,209 B2 | 11/2013 | Nishitani et al. | |
| 8,585,666 B2 | 11/2013 | Weisman | |
| 8,758,569 B2 | 6/2014 | Aberg et al. | |
| 8,778,137 B2 | 7/2014 | Nozaki et al. | |
| 8,853,108 B2 | 10/2014 | Ahoniemi | |
| 8,865,965 B2 | 10/2014 | Sato et al. | |
| 8,906,275 B2 | 12/2014 | Davis | |
| 9,095,477 B2 | 8/2015 | Yamaguchi et al. | |
| 9,156,229 B2 | 10/2015 | Noda et al. | |
| 9,205,005 B2 | 12/2015 | Kikuchi et al. | |
| 9,453,292 B2 | 9/2016 | Sommer et al. | |
| 9,453,303 B2 | 9/2016 | Aberg | |
| 9,732,454 B2 | 8/2017 | Davis | |
| 9,750,651 B2 | 9/2017 | Bianchi et al. | |
| 9,770,371 B2 | 9/2017 | Kanya et al. | |
| 9,877,876 B2 | 1/2018 | Huang | |
| 9,903,070 B2 | 2/2018 | Mourad et al. | |
| 9,993,369 B2 | 6/2018 | Xu | |
| 10,123,916 B2 | 11/2018 | Weisman et al. | |
| 10,190,244 B2 | 1/2019 | Ashraf | |
| 10,639,212 B2 | 5/2020 | Kanya et al. | |
| 10,858,768 B2 | 12/2020 | Ashraf et al. | |
| 11,383,481 B2 | 7/2022 | Sommer et al. | |
| 11,969,325 B2 | 4/2024 | Ashraf | |
| 2001/0029141 A1 | 10/2001 | Mizutani | |
| 2002/0043369 A1 | 4/2002 | Vinegar et al. | |
| 2002/0049418 A1 * | 4/2002 | London Brown | A61F 13/15203 428/340 |
| 2002/0119720 A1 | 8/2002 | Arora et al. | |
| 2002/0153271 A1 | 10/2002 | Mcmanus | |
| 2002/0193032 A1 | 12/2002 | Newkirk et al. | |
| 2003/0085013 A1 | 5/2003 | Burazin et al. | |
| 2003/0093045 A1 | 5/2003 | Erdman | |
| 2003/0119404 A1 | 6/2003 | Belau | |
| 2003/0125687 A1 | 7/2003 | Gubernick et al. | |
| 2003/0149410 A1 * | 8/2003 | Kudo | A61F 13/513 604/385.03 |
| 2003/0161904 A1 | 8/2003 | Geus et al. | |
| 2003/0187415 A1 * | 10/2003 | Kudo | A61F 13/15203 604/385.03 |
| 2003/0203162 A1 | 10/2003 | Fenwick | |
| 2003/0203196 A1 | 10/2003 | Trokhan et al. | |
| 2003/0203691 A1 | 10/2003 | Fenwick et al. | |
| 2003/0211802 A1 | 11/2003 | Keck et al. | |
| 2003/0213620 A1 | 11/2003 | Krueger | |
| 2004/0005457 A1 | 1/2004 | Delucia et al. | |
| 2004/0059309 A1 | 3/2004 | Nortman | |
| 2004/0092902 A1 * | 5/2004 | Hoffman | A61F 13/8405 604/385.01 |
| 2004/0126601 A1 | 7/2004 | Kramer et al. | |
| 2005/0148971 A1 | 7/2005 | Kuroda et al. | |
| 2006/0021536 A1 * | 2/2006 | Song | A61F 13/15203 101/483 |
| 2006/0025735 A1 * | 2/2006 | Berg, Jr. | A61F 13/511 604/385.01 |
| 2006/0025736 A1 * | 2/2006 | Berg, Jr. | A61F 13/84 604/385.01 |
| 2006/0025737 A1 * | 2/2006 | Song | A61F 13/15203 604/385.01 |
| 2006/0087053 A1 | 4/2006 | Odonnell | |
| 2006/0105075 A1 | 5/2006 | Otsubo | |
| 2006/0160453 A1 * | 7/2006 | Suh | A61B 46/40 442/79 |
| 2006/0189954 A1 | 8/2006 | Kudo | |
| 2007/0026753 A1 | 2/2007 | Neely | |
| 2007/0045143 A1 | 3/2007 | Clough | |
| 2007/0045144 A1 | 3/2007 | Wheeler | |
| 2007/0179466 A1 | 8/2007 | Tremblay | |

(56) References Cited

U.S. PATENT DOCUMENTS

| | | |
|---|---|---|
| 2007/0298214 A1 | 12/2007 | Noda et al. |
| 2007/0298667 A1 | 12/2007 | Noda et al. |
| 2008/0149292 A1 | 6/2008 | Scherb |
| 2008/0220161 A1 | 9/2008 | Sommer et al. |
| 2009/0068389 A1* | 3/2009 | Maule ............... D21H 19/82 428/40.1 |
| 2009/0240222 A1 | 9/2009 | Tomoko et al. |
| 2010/0036346 A1 | 2/2010 | Hammons |
| 2010/0048072 A1 | 2/2010 | Kauschke |
| 2010/0062672 A1 | 3/2010 | Fare |
| 2010/0224356 A1 | 9/2010 | Moore |
| 2011/0073513 A1 | 3/2011 | Weisman et al. |
| 2011/0087184 A1* | 4/2011 | Wohlke ............ A61F 13/51104 604/360 |
| 2011/0119850 A1 | 5/2011 | Mallory et al. |
| 2011/0123775 A1 | 5/2011 | Westwood |
| 2011/0137624 A1 | 6/2011 | Weisman et al. |
| 2011/0250378 A1 | 10/2011 | Eaton |
| 2011/0319846 A1* | 12/2011 | Rinnert ................ A61F 13/511 604/366 |
| 2012/0004633 A1 | 1/2012 | R, Marcelo et al. |
| 2012/0196091 A1 | 8/2012 | Mizutani et al. |
| 2012/0238979 A1 | 9/2012 | Weisman et al. |
| 2012/0238982 A1 | 9/2012 | Weisman et al. |
| 2012/0315440 A1 | 12/2012 | Ichikawa et al. |
| 2012/0316532 A1* | 12/2012 | McCormick ...... A61F 13/51104 604/385.01 |
| 2013/0112584 A1 | 5/2013 | Gaspari |
| 2013/0139960 A1 | 6/2013 | Maruyama |
| 2013/0167305 A1 | 7/2013 | Weisman et al. |
| 2013/0171421 A1 | 7/2013 | Weisman |
| 2013/0178811 A1* | 7/2013 | Kikuchi ............ A61F 13/51104 604/379 |
| 2013/0320584 A1 | 12/2013 | Davis et al. |
| 2014/0044934 A1* | 2/2014 | Bills ........................ B32B 5/26 428/196 |
| 2014/0088535 A1* | 3/2014 | Xu ................... A61F 13/15731 604/366 |
| 2014/0127460 A1 | 5/2014 | Xu |
| 2014/0163502 A1 | 6/2014 | Arizti |
| 2014/0202711 A1 | 7/2014 | Scott et al. |
| 2014/0234575 A1 | 8/2014 | Mitsuno |
| 2014/0276517 A1 | 9/2014 | Chester |
| 2014/0296815 A1 | 10/2014 | Takken |
| 2014/0305570 A1 | 10/2014 | Matsunaga |
| 2014/0324009 A1 | 10/2014 | Lee |
| 2014/0343526 A1* | 11/2014 | Knapmeyer ....... D04H 1/43828 428/196 |
| 2014/0358101 A1 | 12/2014 | Kanya et al. |
| 2015/0173967 A1 | 6/2015 | Kreuzer |
| 2015/0209202 A1 | 7/2015 | Weisman et al. |
| 2015/0250662 A1* | 9/2015 | Isele ................... A61F 13/5121 604/378 |
| 2015/0257943 A1 | 9/2015 | Noel |
| 2015/0265473 A1 | 9/2015 | Hammons et al. |
| 2015/0282999 A1 | 10/2015 | Arizti |
| 2016/0067119 A1 | 3/2016 | Weisman |
| 2016/0074254 A1* | 3/2016 | Orr ................... A61F 13/5116 428/161 |
| 2016/0074259 A1* | 3/2016 | Rosati .............. A61F 13/15203 604/378 |
| 2016/0076182 A1* | 3/2016 | Strube .................. B32B 38/06 28/134 |
| 2016/0076184 A1* | 3/2016 | Orr ................... A61F 13/53743 428/178 |
| 2016/0106633 A1 | 4/2016 | Nagata |
| 2016/0129661 A1 | 5/2016 | Arora |
| 2016/0136009 A1 | 5/2016 | Weisman |
| 2016/0235597 A1 | 8/2016 | Ehrnsperger et al. |
| 2016/0244915 A1* | 8/2016 | Mohammadi .......... D21H 17/02 |
| 2016/0362825 A1 | 12/2016 | Novarino et al. |
| 2017/0009401 A1* | 1/2017 | O'Brien Stickney .. D21H 27/30 |
| 2017/0014281 A1 | 1/2017 | Xie |
| 2017/0014291 A1 | 1/2017 | Tao et al. |
| 2017/0027774 A1 | 2/2017 | Ashraf |
| 2017/0029993 A1 | 2/2017 | Ashraf |
| 2017/0029994 A1* | 2/2017 | Ashraf ............. A61F 13/51104 |
| 2017/0056256 A1* | 3/2017 | Smith ................. A61F 13/515 |
| 2017/0121873 A1 | 5/2017 | Kimura et al. |
| 2017/0137980 A1 | 5/2017 | Kauschke et al. |
| 2017/0151103 A1* | 6/2017 | Bianchi ............ A61F 13/51394 |
| 2017/0175313 A1 | 6/2017 | Song et al. |
| 2017/0191198 A1* | 7/2017 | Ashraf ..................... D01F 6/06 |
| 2017/0258650 A1 | 9/2017 | Rosati |
| 2017/0314163 A1 | 11/2017 | Sommer et al. |
| 2017/0348163 A1 | 12/2017 | Lakso |
| 2018/0098893 A1 | 4/2018 | Viens |
| 2018/0168893 A1 | 6/2018 | Ashraf |
| 2018/0214318 A1 | 8/2018 | Ashraf |
| 2018/0214321 A1 | 8/2018 | Ashraf |
| 2018/0216269 A1* | 8/2018 | Ashraf ................... D04H 3/018 |
| 2018/0216270 A1 | 8/2018 | Ashraf |
| 2018/0216271 A1 | 8/2018 | Ashraf |
| 2018/0344544 A1 | 12/2018 | Tally |
| 2019/0003079 A1 | 1/2019 | Ashraf |
| 2019/0003080 A1 | 1/2019 | Ashraf |
| 2019/0112737 A1 | 4/2019 | Ashraf |
| 2019/0298587 A1* | 10/2019 | Ashraf ............. A61F 13/15707 |
| 2019/0388578 A1 | 12/2019 | Aviles |
| 2020/0038262 A1 | 2/2020 | Aviles et al. |
| 2020/0054501 A1 | 2/2020 | Seto et al. |
| 2020/0299881 A1 | 9/2020 | Ashraf |
| 2021/0040661 A1 | 2/2021 | Ashraf et al. |
| 2021/0077319 A1 | 3/2021 | Weber et al. |
| 2021/0214858 A1 | 7/2021 | Sommer et al. |
| 2022/0074094 A1 | 3/2022 | Ashraf et al. |

FOREIGN PATENT DOCUMENTS

| | | | |
|---|---|---|---|
| CN | 1685099 A | 10/2005 | |
| CN | 1722997 A * | 1/2006 | ....... A61F 13/51496 |
| CN | 101443499 A | 5/2009 | |
| CN | 103108616 A | 5/2013 | |
| CN | 104507436 A | 4/2015 | |
| CN | 105473114 A | 4/2016 | |
| CN | 108366888 A | 8/2018 | |
| CN | 110022822 A | 7/2019 | |
| EA | 2660377 B1 | 4/2014 | |
| EP | 1227181 A2 | 7/2002 | |
| EP | 1234906 | 8/2002 | |
| EP | 1323400 A2 | 7/2003 | |
| EP | 1338262 A1 | 8/2003 | |
| EP | 3210584 A1 | 8/2017 | |
| JP | S4827070 A | 4/1973 | |
| JP | S4853061 A | 7/1973 | |
| JP | 61111993 U * | 7/1986 | |
| JP | H04327255 A | 11/1992 | |
| JP | 2003052752 A | 2/2003 | |
| JP | 2006510456 A | 3/2006 | |
| JP | 2008509786 A | 4/2008 | |
| JP | 2009136349 A | 6/2009 | |
| JP | 2011015707 A | 1/2011 | |
| JP | 2012075638 A | 4/2012 | |
| JP | 5399174 B2 | 11/2013 | |
| JP | 2013244256 A | 12/2013 | |
| JP | 2014070299 A | 4/2014 | |
| JP | 2014097257 A | 5/2014 | |
| JP | 2014515986 A | 7/2014 | |
| JP | 2014188042 A | 10/2014 | |
| JP | 2014234345 A | 12/2014 | |
| JP | 2019044294 A * | 3/2019 | |
| KR | 100988698 B1 | 10/2010 | |
| RU | 2388860 C2 | 5/2010 | |
| WO | WO-9628597 A1 * | 9/1996 | ............ B29C 59/10 |
| WO | 9716751 A1 | 5/1997 | |
| WO | 2003015681 | 2/2003 | |
| WO | 03057117 A1 | 7/2003 | |
| WO | 201286730 A1 | 6/2012 | |
| WO | 2013018846 A1 | 2/2013 | |
| WO | 2013084977 A1 | 6/2013 | |
| WO | 2013099625 A1 | 7/2013 | |
| WO | 2013145966 A1 | 10/2013 | |
| WO | 2015000774 A1 | 1/2015 | |

(56) References Cited

FOREIGN PATENT DOCUMENTS

| WO | 2015073374 A1 | | 5/2015 | | |
| --- | --- | --- | --- | --- | --- |
| WO | WO-2016040101 A1 | * | 3/2016 | ........ | A61F 13/51104 |
| WO | WO-2016040103 A1 | * | 3/2016 | ........ | A61F 13/51104 |
| WO | WO-2016040104 A1 | * | 3/2016 | ........ | A61F 13/51104 |
| WO | WO-2016040118 A1 | * | 3/2016 | ........ | A61F 13/51104 |
| WO | WO-2016073694 A1 | * | 3/2016 | ....... | A61F 13/15203 |
| WO | 2017105997 A1 | | 6/2017 | | |
| WO | 2017110695 A1 | | 6/2017 | | |
| WO | 2020226951 A1 | | 11/2020 | | |

OTHER PUBLICATIONS

All Office Actions; U.S. Appl. No. 18/192,741, filed Mar. 30, 2023.
Unpublished U.S. Appl. No. 18/192,741, filed Mar. 30, 2023, to Arman Ashraf et al.
All Office Actions: U.S. Appl. No. 17/529,345, filed Nov. 18, 2021.
Unpublished U.S. Appl. No. 17/629,345, filed Nov. 18, 2021, to Arman Ashraf et al.
15670MQ PCT Search Report and Written Opinion for PCT/US2020/063525 dated Mar. 18, 2021.
All Office Actions U.S. Appl. No. 15/221,625.
All Office Actions U.S. Appl. No. 15/221,628.
All Office Actions U.S. Appl. No. 16/214,526.
All Office Actions, U.S. Appl. No. 15/221,626.
All Office Actions, U.S. Appl. No. 15/221,624.
All Office Actions, U.S. Appl. No. 17/076,847.
All Office Actions; U.S. Appl. No. 18/301,526, filed Apr. 17, 2023.
Unpublished U.S. Appl. No. 18/301,526, filed Apr. 17, 2023, to Arman Ashraf et al.

* cited by examiner

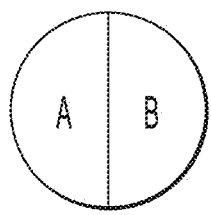 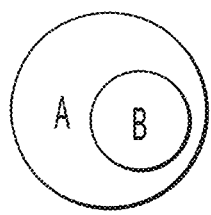 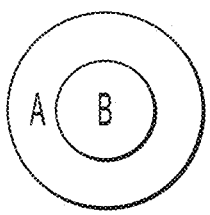
Fig. 13A  Fig. 13B  Fig. 13C
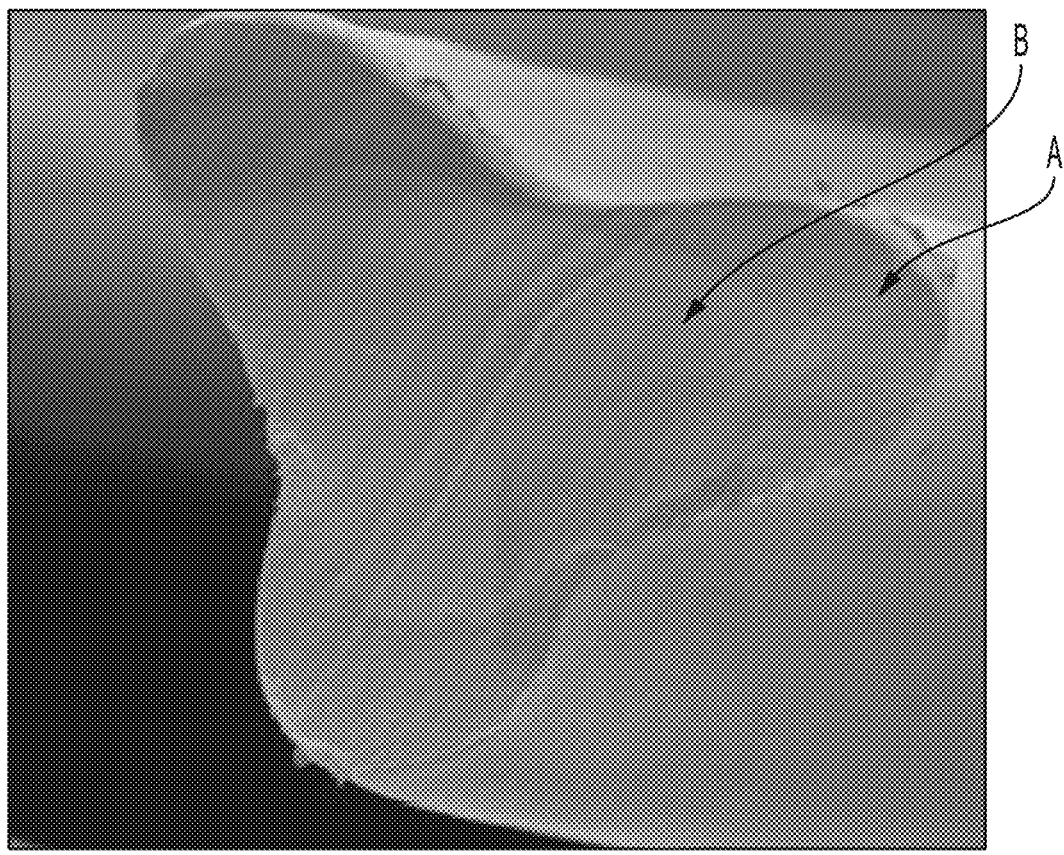

NONWOVEN WEBS WITH VISUALLY DISCERNIBLE PATTERNS AND IMPROVED TEXTURE PERCEPTION

CROSS REFERENCE TO RELATED APPLICATION

This application claims priority, under 35 U.S.C. § 119(e), to U.S. Provisional Patent Application No. 62/946,047, filed on Dec. 10, 2019, the entire disclosure of which is hereby incorporated by reference.

FIELD

The present disclosure is generally directed to nonwoven webs with visually discernible patterns and improved texture perception. The present disclosure is also directed to absorbent articles comprising nonwoven webs with visually discernible patterns and improved texture perception.

BACKGROUND

Nonwoven webs are used in many industries, including the medical, hygiene, and cleaning industries. Absorbent articles comprising nonwoven webs are used in the hygiene industry to contain and absorb bodily exudates (i.e., urine, bowel movements, and menses) in infants, toddlers, children, and adults. Absorbent articles may include, but not be limited to, diapers, pants, adult incontinence products, feminine care products, and absorbent pads. Various components of these absorbent articles comprise one or more nonwoven webs. Some example components that comprise nonwoven webs are outer cover nonwoven materials, topsheets, waistbands, leg cuffs, waist cuffs, ears, belts, and acquisition materials, for example. High quality nonwoven webs that function well for their intended purpose are desired. Manufacturers seek to develop and deliver high quality nonwoven webs as consumers may pay more for absorbent articles with such high quality nonwoven webs. Some factors that contribute to high quality nonwoven webs are texture, perceived absorbency, visual appearance, and softness. Texture, however, is difficult to perceive on white nonwoven webs. It may be desirable to provide white or noncolored nonwoven webs, yet it is difficult to deliver white or noncolored nonwovens with high quality levels of texture, perceived absorbency, and softness. As such, nonwoven webs should be improved.

SUMMARY

The present disclosure provides, in part, nonwoven webs with visually discernable patterns of three-dimensional features that have improved texture perception, improved absorbency perception, and softness. The present disclosure also provides, in part, absorbent articles comprising nonwoven webs with visually discernable patterns of three-dimensional features that have improved texture perception and softness. It is believed that select nonwoven textures may further contribute to perceived absorbency and/or softness. Unfortunately, highly textured nonwoven webs may also negatively impact skin marking and skin redness as topsheet nonwovens. Therefore, create a three-dimensional or three-dimensional like textures that contribute to softness and absorbency perception while not causing skin marking are highly desirable. The present inventors have unexpectedly discovered how a low level of a colorant, a pigment, and/or a dye, when included as a melt additive when forming a master batch used to form filaments of nonwoven webs, provides for greatly enhanced visual texture contrast or improved texture perception. This improved texture perception provides for improved nonwoven webs of the present disclosure. It is noted that while the nonwoven webs of the present disclosure provide improved texture perception, the nonwoven webs are still viewed as "white," non-colored, or without any added colorant, pigment, and/or dye. White or non-colored, or without any added colorant, pigment, and/or dye does not mean TiO2 additives. Thus, the present disclosure provides for unexpected texture perception benefits by using a low level of a colorant, pigment, and/or a dye, while maintaining the level of the colorant, pigment, and/or dye below a level of where it would be viewed by a human eye as having a color other than white. As an example, a low level of a blue colorant may be added when forming a master batch to form filaments of the nonwoven webs to increase the texture perception, while the nonwoven webs still appear white to a human eye.

The visually discernable patterns of three-dimensional features of the nonwoven webs of the present disclosure may comprise one or more first regions and a plurality of second regions. The one or more first regions may be areas where the nonwoven webs are low-basis weight, densified, and/or compressed and the plurality of second regions may be fluffy, high basis weight areas. The plurality of second regions may increase softness in the nonwoven webs. This combination of improved texture perception and softness creates premium nonwoven webs that are highly desired.

The present disclosure is directed, in part, to a nonwoven web for an absorbent article. The nonwoven web, such as a spunbond nonwoven web, comprises a first surface, a second surface, and a visually discernible pattern of three-dimensional features on the first surface or the second surface. The three-dimensional features comprise one or more first regions and a plurality of second regions. The one or more first regions have a first value of an average intensive property. The plurality second regions have a second value of the average intensive property. The first value and the second value are different and are both greater than zero. The nonwoven web has a Single Layer Chroma value in the range of about 1.0 to about 3.5, according to the Delta Chroma and Single Layer Chroma Test. The nonwoven web has a Delta Chroma value in the range of about +0.1 to about +3.5, according to the Delta Chroma and Single Layer Chroma Test.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 13A is a schematic drawing illustrating a cross-section of a filament made with a primary component A and a secondary component B in a side-by-side arrangement;

FIG. 13B is a schematic drawing illustrating a cross-section of a filament made with a primary component A and a secondary component B in an eccentric sheath/core arrangement;

FIG. 13C is a schematic drawing illustrating a cross-section of a filament made with a primary component A and a secondary component B in a concentric sheath/core arrangement;

DETAILED DESCRIPTION

Various non-limiting forms of the present disclosure will now be described to provide an overall understanding of the principles of the structure, function, manufacture, and use of the nonwoven webs with visually discernable patterns and improved texture perception disclosed herein. One or more examples of these non-limiting forms are illustrated in the accompanying drawings. Those of ordinary skill in the art will understand that the nonwoven webs with visually discernable patterns and improved texture perception described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Prior to a discussion of the nonwoven webs with visually discernable patterns absorbent articles and their components and features will be discussed as one possible use of the nonwoven webs. It will be understood that the nonwoven webs with visually discernable patterns also have other uses in other products, such as in the medical field, the cleaning and/or dusting field, and/or the wipes field, for example.

General Description of an Absorbent Article

Figure 1:
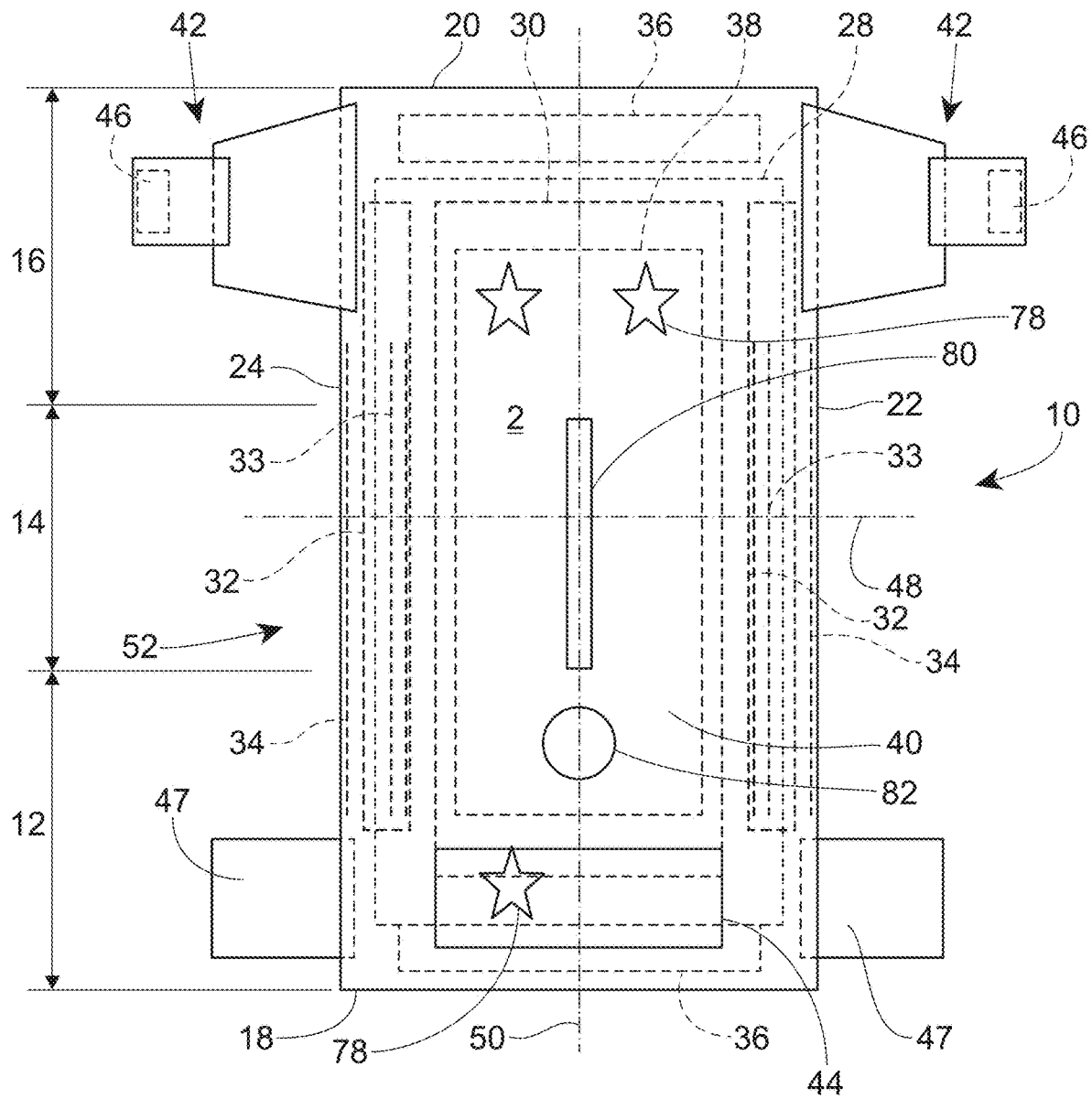
FIG. 1 is a plan view of an example absorbent article in the form of a taped diaper, garment-facing surface facing the viewer, in a flat laid-out state.
Figure 2:
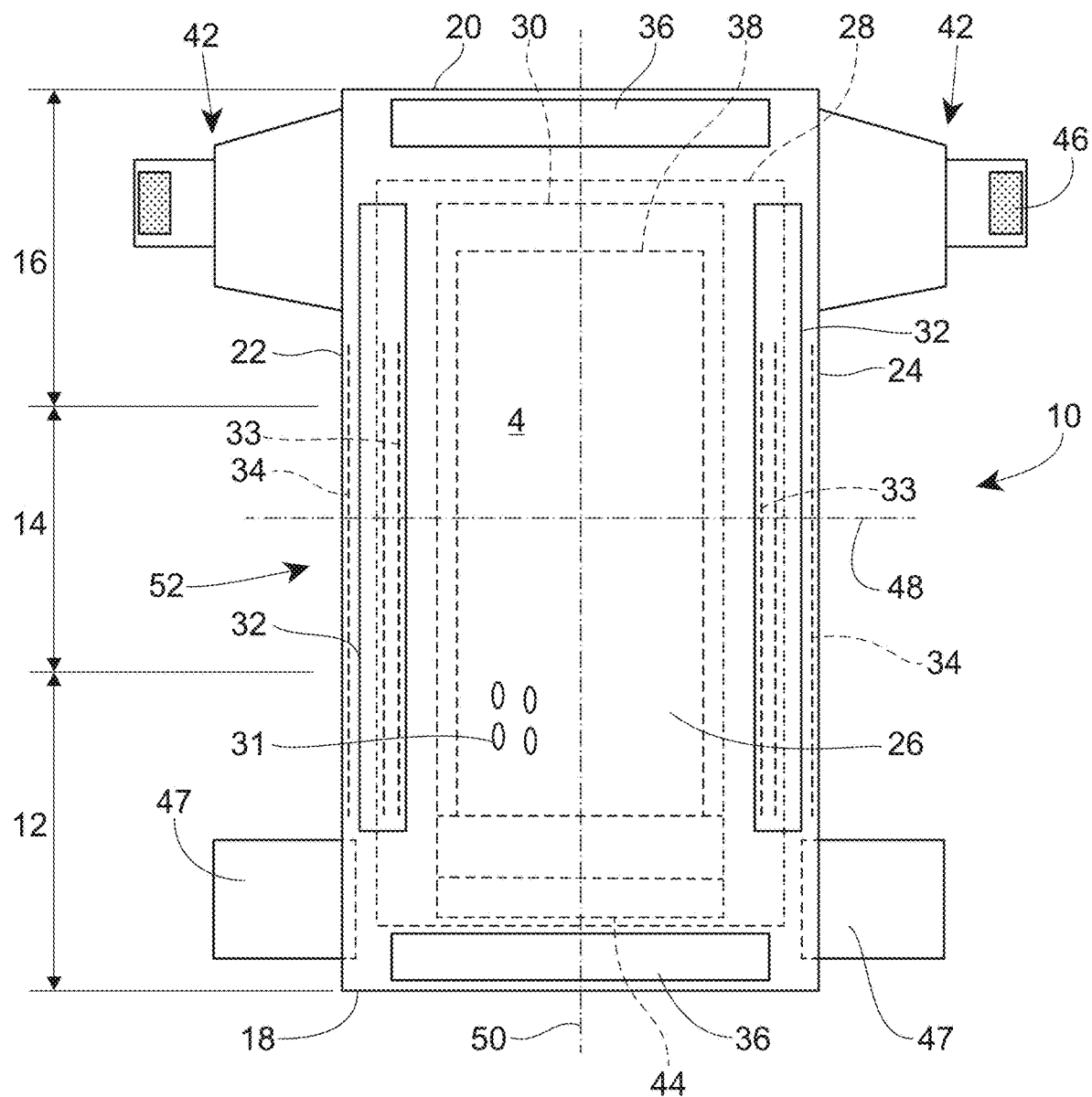
FIG. 2 is a plan view of the example absorbent article of FIG. 1, wearer-facing surface facing the viewer, in a flat laid-out state.
Figure 3:
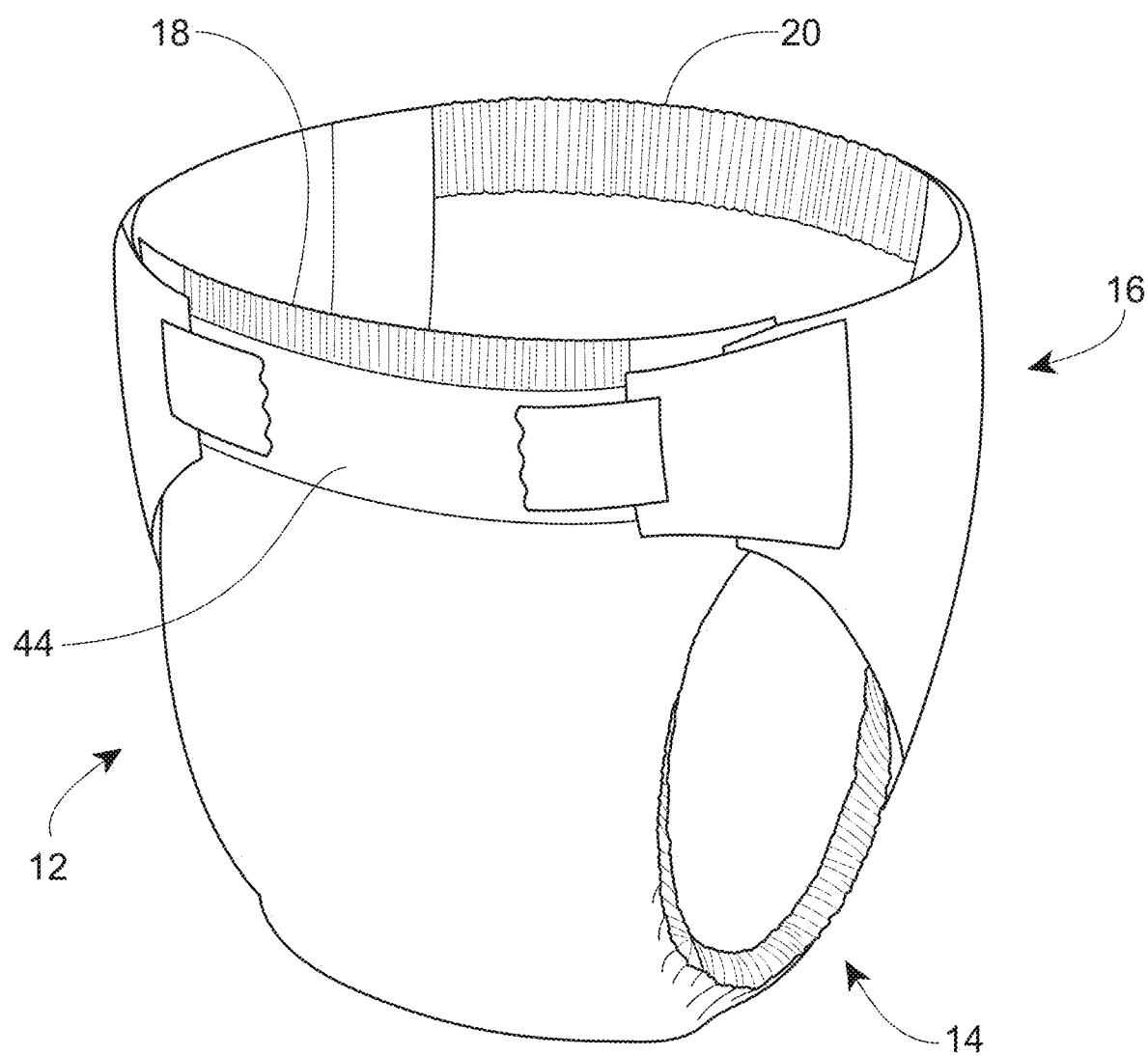
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover nonwoven material 40, such as a nonwoven web, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. Instead of two front ears 47, the absorbent article 10 may have a single piece front belt that may function as a landing zone as well. The absorbent article 10 may have a central lateral (or transverse) axis 48 and a central longitudinal axis 50. The central lateral axis 48 extends perpendicular to the central longitudinal axis 50.

Figure 4:
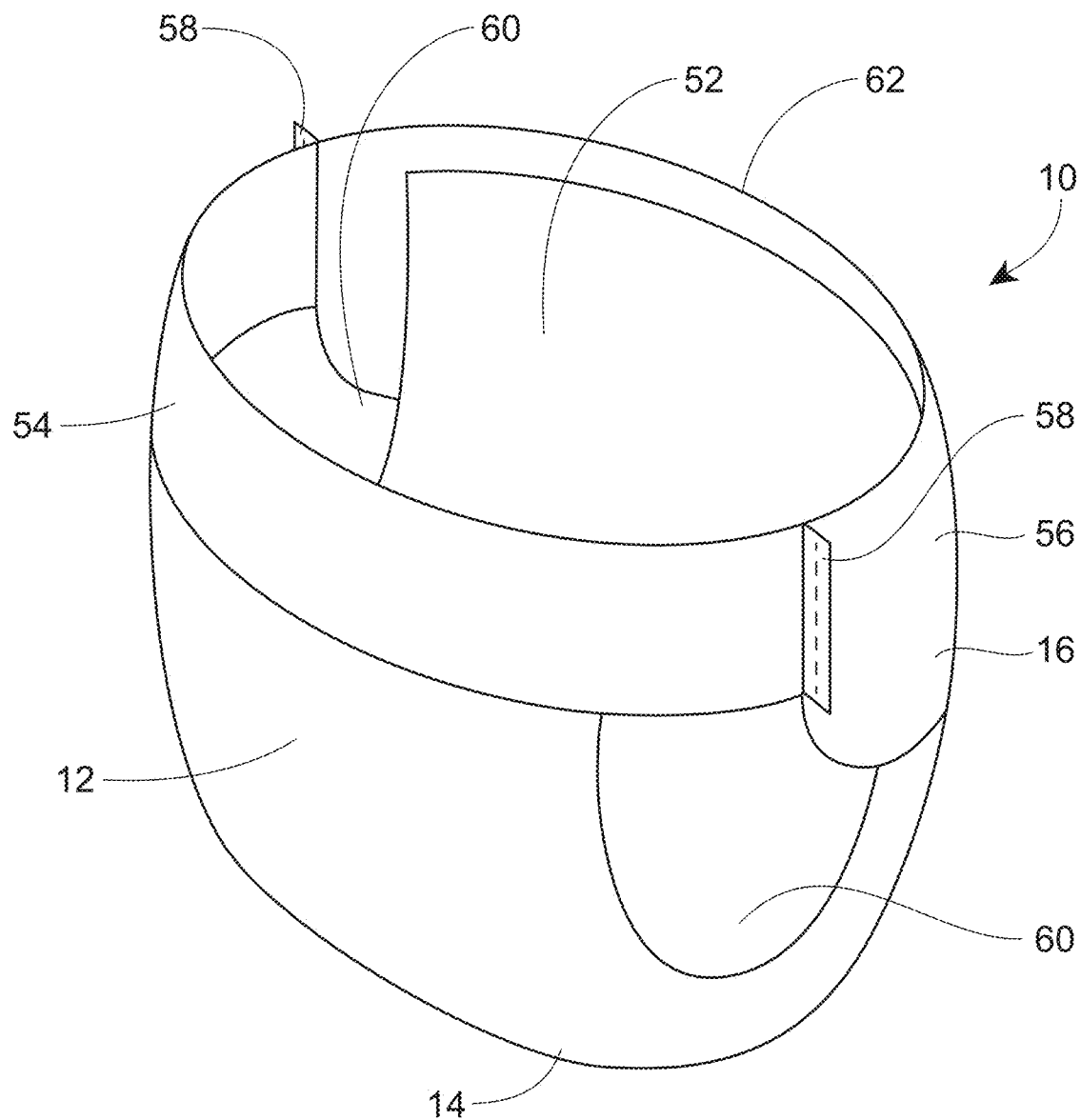
FIG. 4 is a front perspective view of an absorbent article in the form of a pant.
Figure 5:
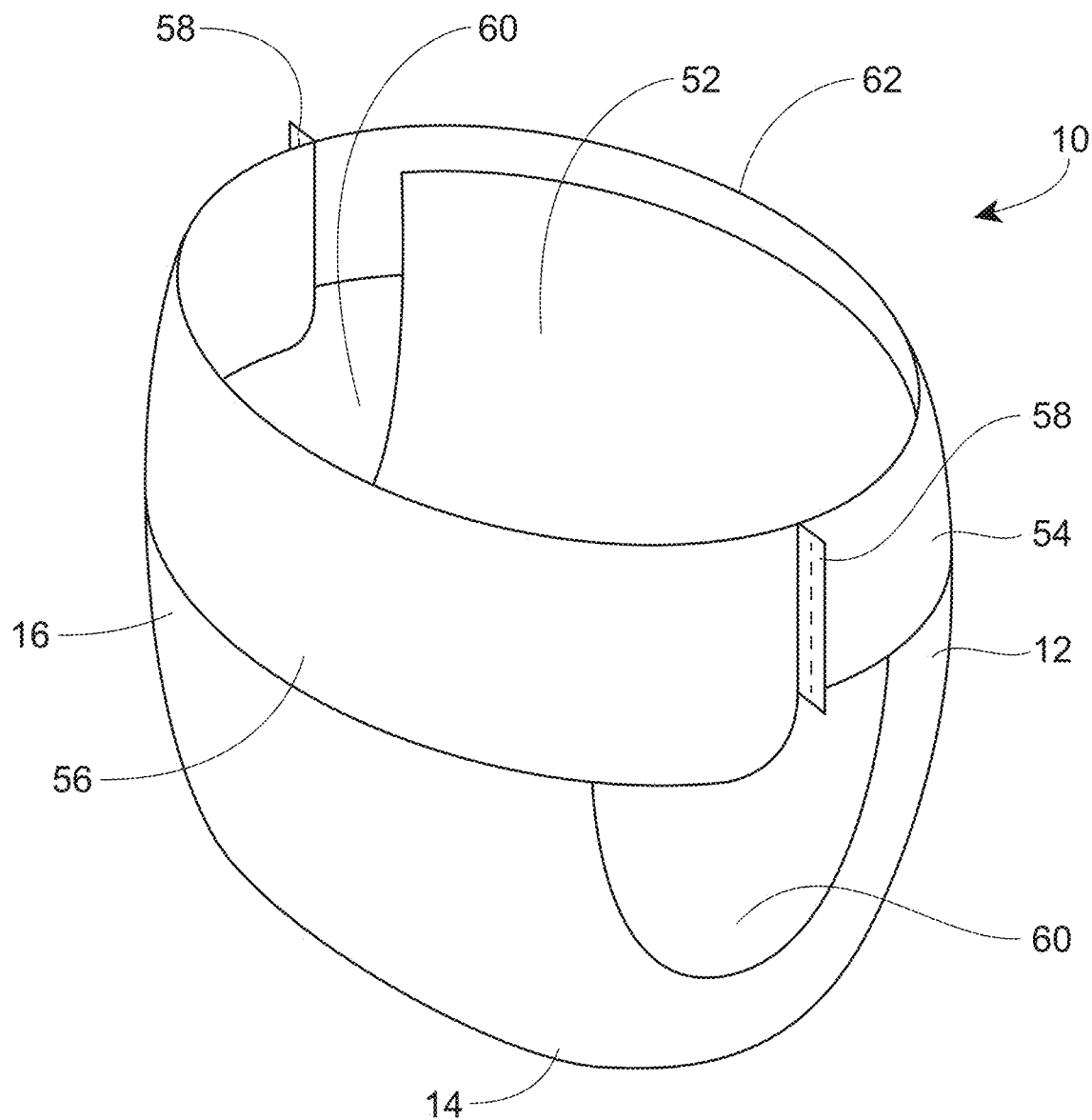
FIG. 5 is a rear perspective view of the absorbent article of FIG. 4.
Figure 6:
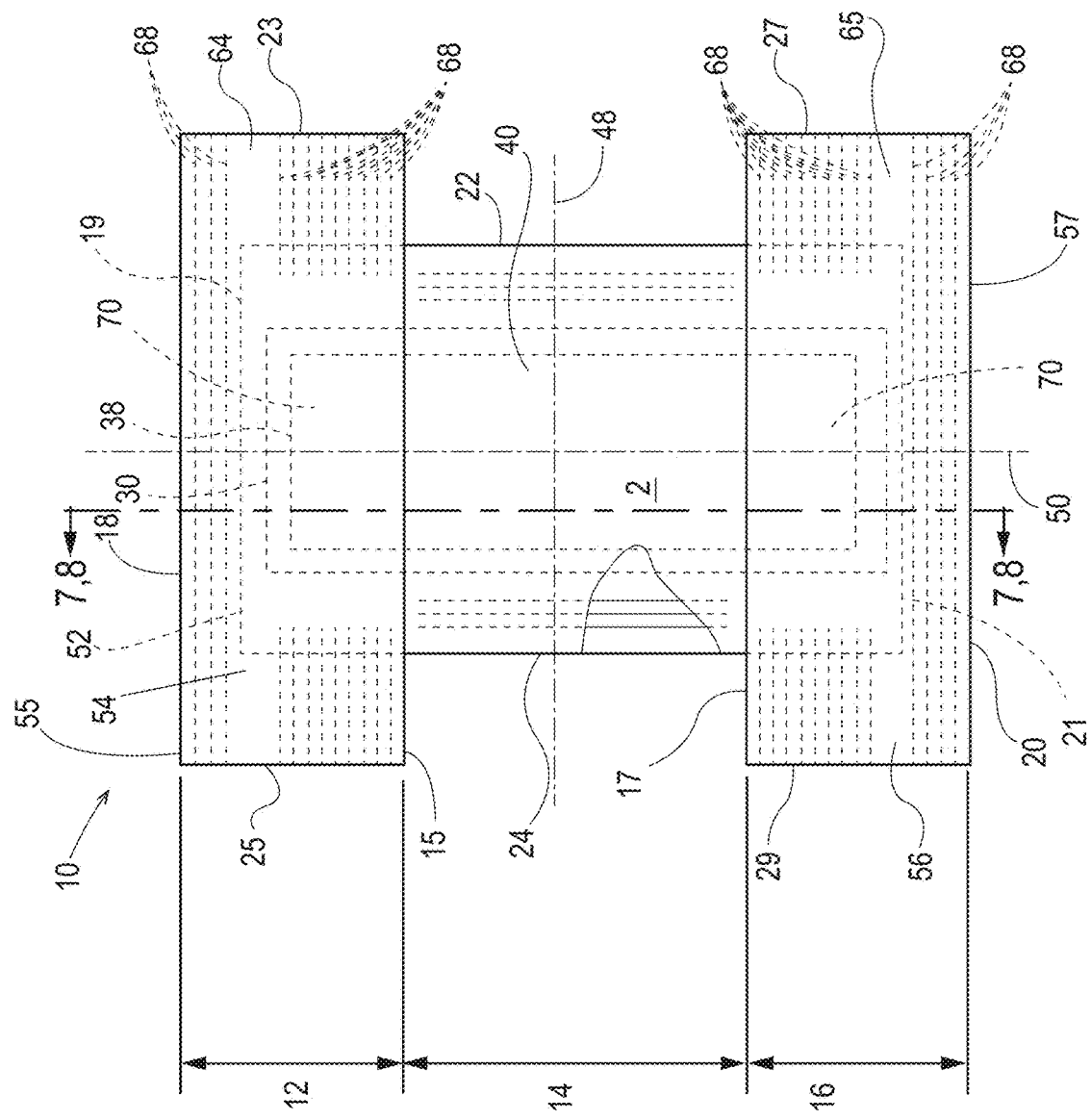
FIG. 6 is a plan view of the absorbent article of FIG. 4, laid flat, with a garment-facing surface facing the viewer.
Figure 7:
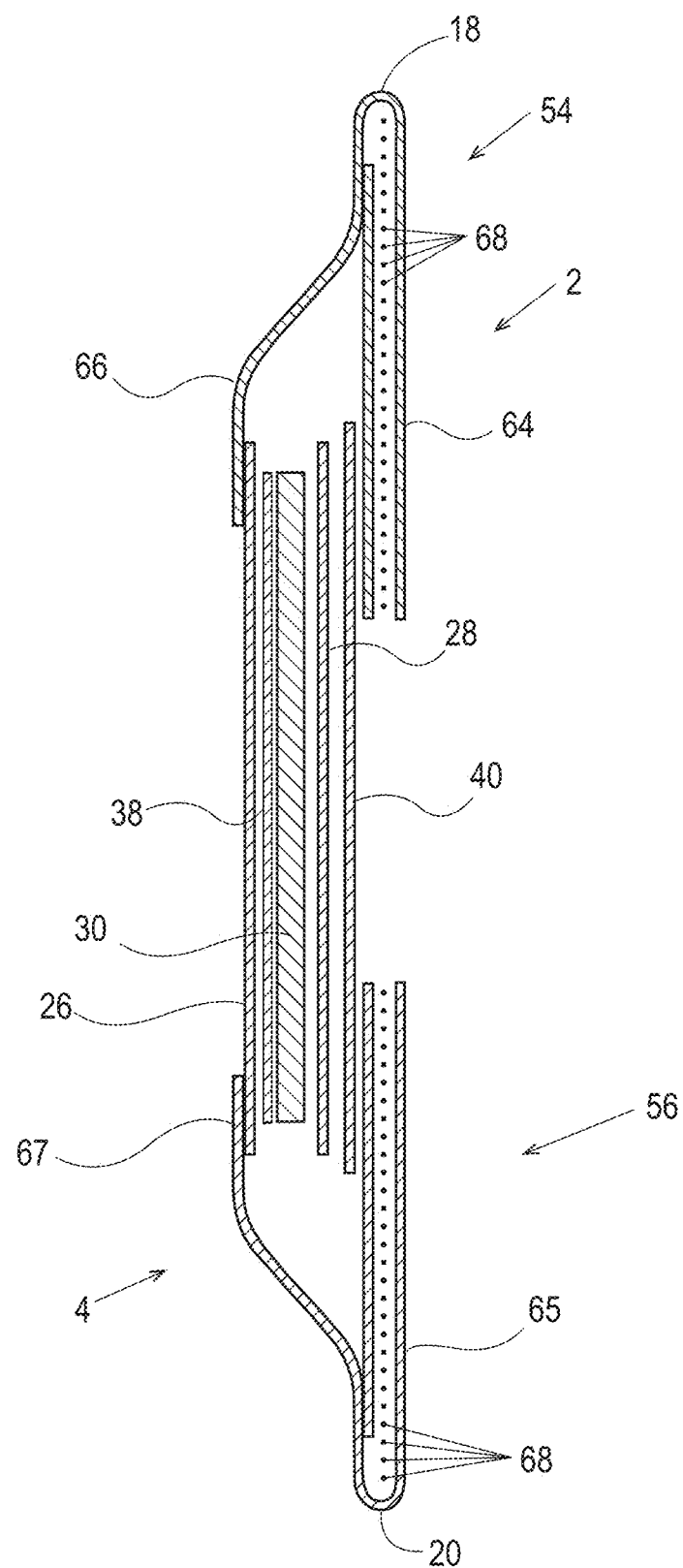
FIG. 7 is a cross-sectional view of the absorbent article taken about line 7-7 of FIG. 6.
Figure 8:
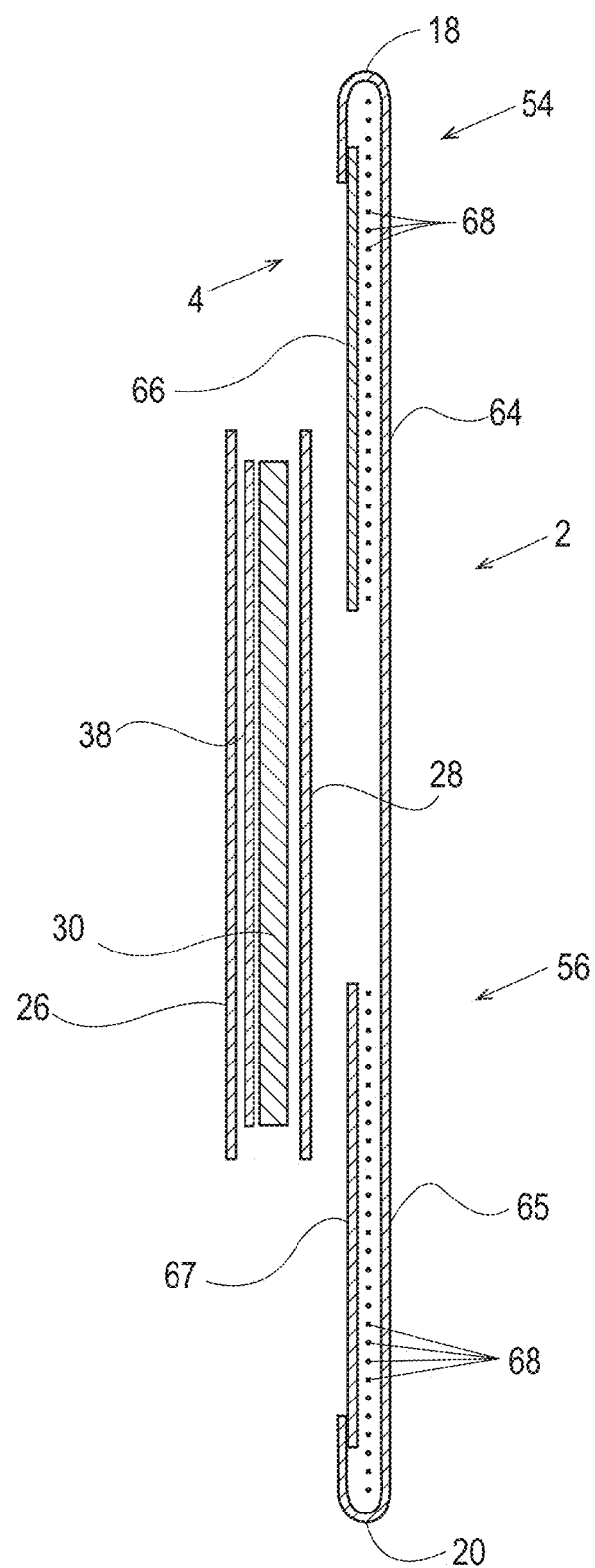
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24.

The nonwoven webs with visually discernable patterns and improved texture perception may be used as nonwoven components of the belts, or portions thereof.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven webs, woven or nonwoven webs of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The nonwoven webs with visually discernable patterns and improved texture perception may be used as nonwoven topsheets, or portions thereof.

Backsheet

The backsheet 28 is generally that portion of the absorbent article 10 positioned proximate to the garment-facing surface of the absorbent core 30. The backsheet 28 may be joined to portions of the topsheet 26, the outer cover nonwoven material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Nonwoven Material

The outer cover nonwoven material (sometimes referred to as a backsheet nonwoven) 40 may comprise one or more nonwoven materials joined to the backsheet 28 and that covers the backsheet 28. The outer cover nonwoven material 40 forms at least a portion of the garment-facing surface 2 of the absorbent article 10 and effectively "covers" the backsheet 28 so that film is not present on the garment-facing surface 2. The nonwoven webs with visually discernable patterns and improved texture perception may be used as the outer cover nonwoven material, or portions thereof.

Absorbent Core

Figure 9:
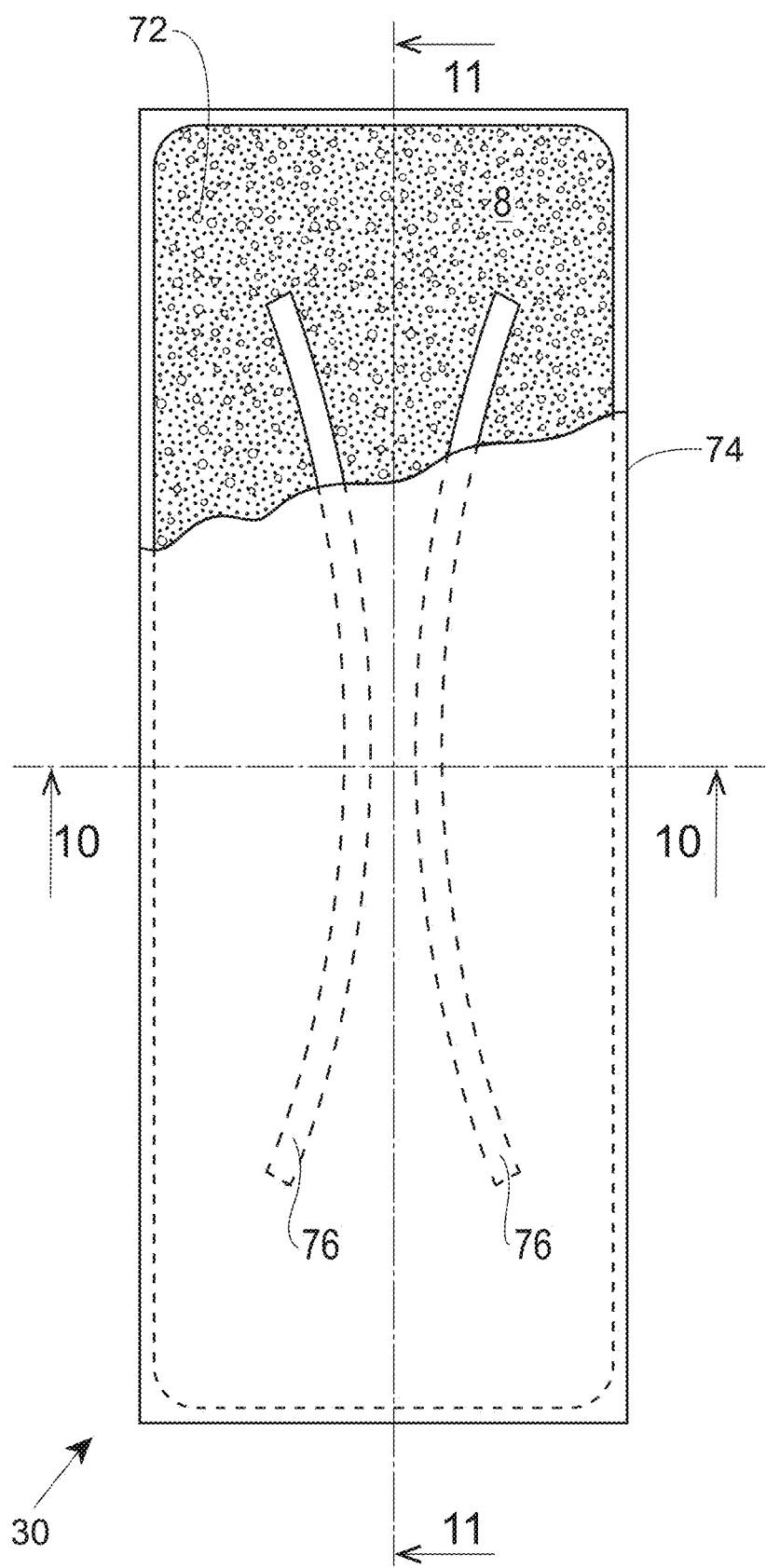
FIG. 9 is a plan view of an example absorbent core or an absorbent article.
Figure 10:
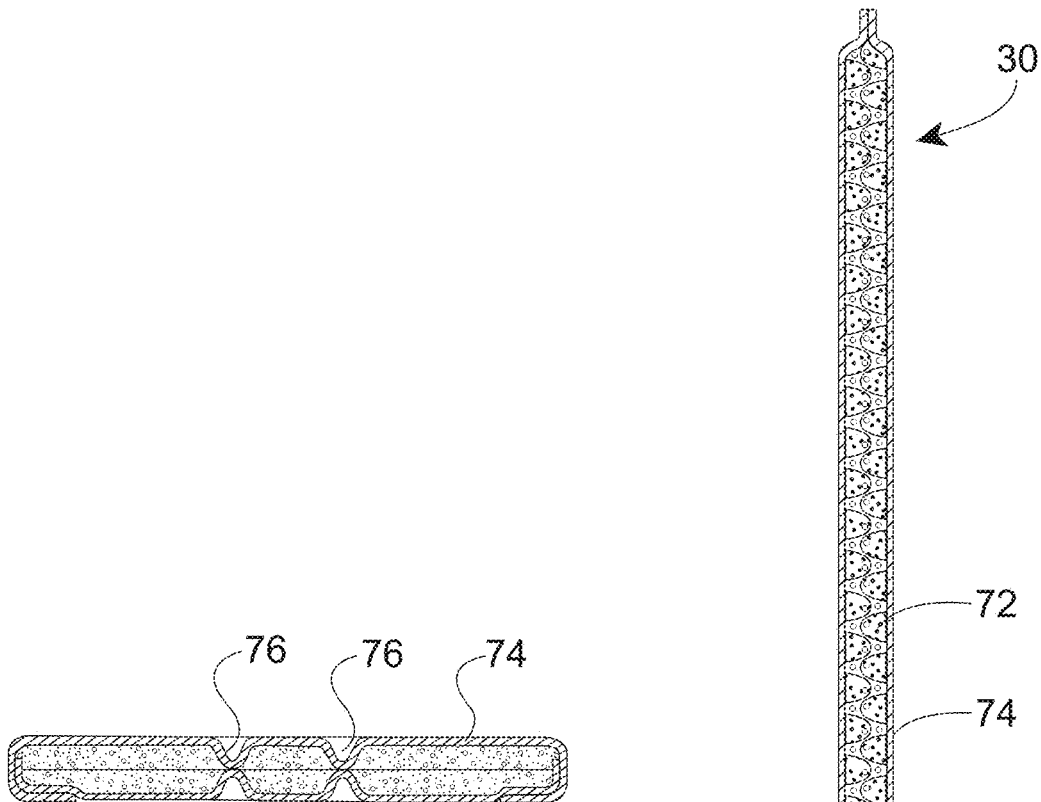
FIG. 10 is a cross-sectional view, taken about line 10-10, of the absorbent core of FIG. 9.
Figure 11:
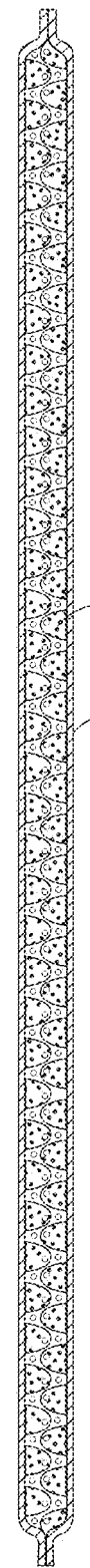
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

The nonwoven webs with visually discernable patterns and improved texture perception may be used as nonwoven components of the barrier leg cuffs, or portions thereof.

Waistband

Referring to FIGS. 1 and 2, the absorbent article 10 may comprise one or more elastic waistbands 36 or non-elastic waistband. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

The nonwoven webs with visually discernable patterns and improved texture perception may be used as nonwoven components of the waistband, or portions thereof.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven webs, foams, cellulosic materials, cross-linked cellulosic materials, air laid cellulosic nonwoven webs, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven web and as second acquisition material may comprise a cross-linked cellulosic material. The nonwoven webs with visually discernable patterns and improved texture perception may be used as nonwoven components of the acquisition materials, or portions thereof.

Landing Zone

Referring to FIGS. 1 and 2, the absorbent article 10 may have a landing zone area 44 that is formed in a portion of the garment-facing surface 2 of the outer cover nonwoven material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover nonwoven material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

The nonwoven webs with visually discernable patterns and improved texture perception may be used as nonwoven components of the landing zone, or portions thereof.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven web and a second nonwoven web. The elastic film may or may not be apertured. The ears may be shaped. The ears may be integral (e.g., extension of the outer cover nonwoven material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

The nonwoven webs with visually discernable patterns and improved texture perception may be used as nonwoven components of the front and back ears, or portions thereof.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise nonwoven webs, polymeric films, and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate number of absorbent articles per package. By packaging the absorbent articles under compression, caregivers can easily handle and store the packages, while also providing distribution savings to manufacturers owing to the size of the packages. The nonwoven webs with visually discernable patterns and improved texture perception may be used as nonwoven components of the packages, or portions thereof.

Sanitary Napkin

Figure 12:
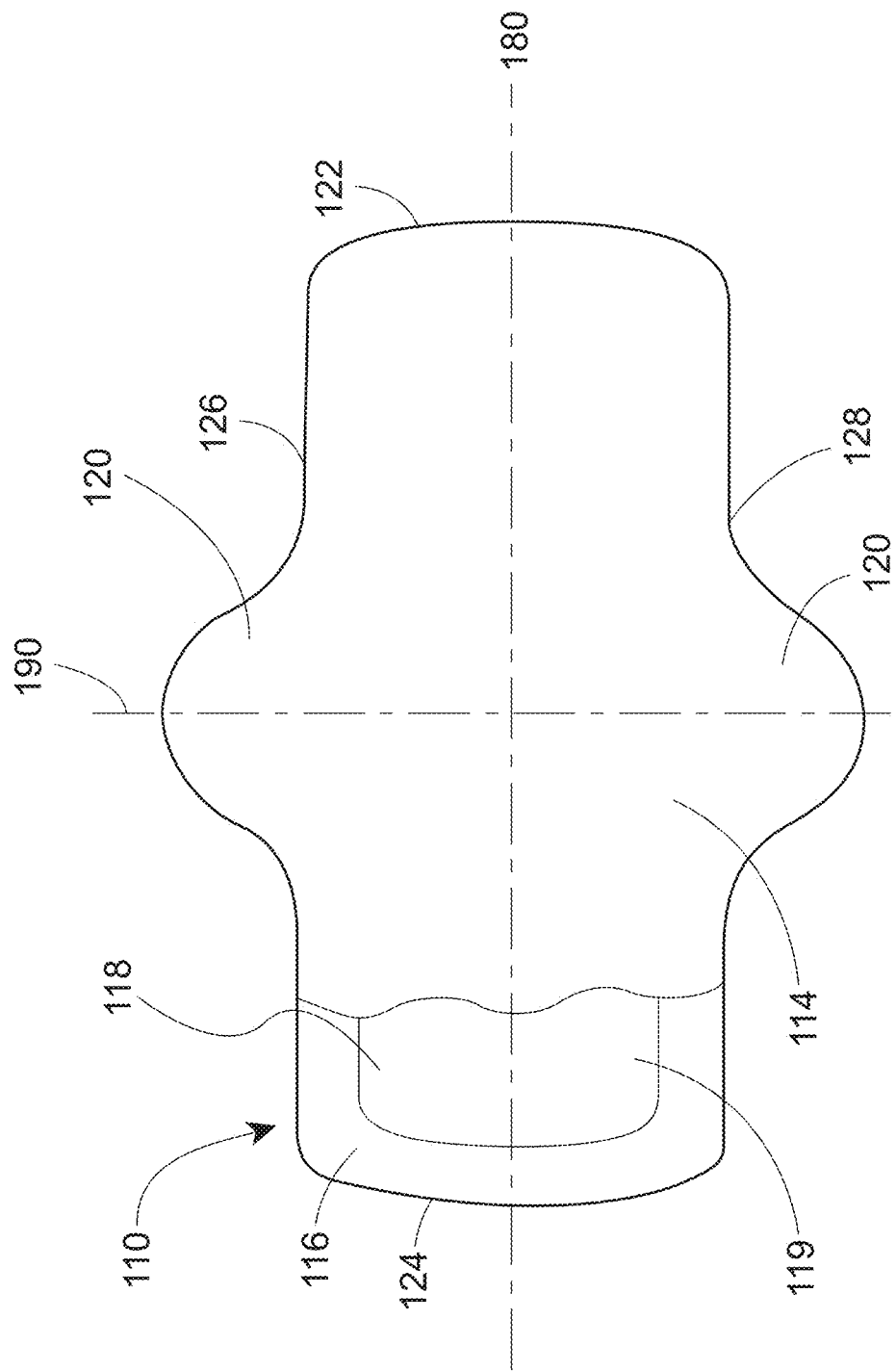
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

The nonwoven webs with visually discernable patterns and improved texture perception may be used as nonwoven components of sanitary napkins, or portions thereof.

Nonwoven Webs with Visually Discernible Patterns

The nonwoven webs with visually discernable patterns are now discussed. The nonwoven webs with visually discernible patterns and improved texture perception will be discussed later. The visually discernable patterns may be formed by three-dimensional features. Such nonwoven webs may be used as various components of, or portions of components of, absorbent articles, such as topsheets, wings, outer cover nonwoven materials, belts, waistbands, leg cuffs, waist cuffs, landing zones, acquisition materials, and/or ears, for example.

Any of the nonwoven webs of the present disclosure may be through-air bonded such that bonds occur at individual fiber intersections as hot air is passed through the nonwoven webs. Through-air bonding may help maintain softness in the nonwoven webs compared to more conventional calendar bonding. Other methods of bonding may include calendar point bonding, ultrasonic bonding, latex bonding, hydroentanglement, resin bonding, and/or combinations thereof.

Any of the nonwoven webs of the present disclosure may comprise portions of, or all of, components of absorbent articles. An absorbent article, as discussed above, may comprise a liquid permeable topsheet, a liquid impermeable backsheet, and an absorbent core positioned at least partially intermediate the topsheet and the backsheet. The absorbent article may comprise an outer cover nonwoven material forming at least a portion of a garment-facing surface of the absorbent article. The outer cover nonwoven material and/or the topsheet may comprise the nonwoven webs of the present disclosure. Other components of absorbent articles, or portions thereof, may also comprise the nonwoven webs of the present disclosure, such as leg cuffs, waist cuffs, belts, landing zones, waistbands, and/or ears, for example.

A nonwoven web for an absorbent article is provided. The nonwoven web may comprise a first surface, a second surface, and a visually discernible pattern of three-dimensional features on the first surface or the second surface. The three-dimensional features may comprise one or more first regions and a plurality of second regions. The one or more first regions are different than the plurality of second regions in a value of an average intensive property, wherein the average intensity property is basis weight, volumetric density, and/or caliper.

The nonwoven webs comprising the visually discernable patterns of three-dimensional features may have a basis weight in the range of about 10 gsm to about 100 gsm, about 10 gsm to about 60 gsm, about 15 gsm to about 50 gsm, about 15 gsm to about 45 gsm, about 20 gsm to about 40 gsm, about 20 gsm to about 35 gsm, about 20 gsm to about 30 gsm, according to the Basis Weight Test herein, and specifically reciting all 0.1 gsm increments within the specified ranges and all ranges formed therein or thereby.

The visually discernable pattern of three-dimensional features may be formed in a nonwoven web by embossing, hydroentangling, or by using a structured forming belt for fiber laydown. Using embossing or hydroentangling, the first regions or the second regions may be embossed or hydroentangled to form the pattern. The structured forming belt is discussed herein.

Materials

The nonwoven webs of the present disclosure may be formed by a dry-laid process using short staple fibers and mechanical web formation, such as a carding process. The resulting webs may be bonded using irregular pattern thermal embossing or hydroforming/hydroentangling processes. The nonwoven webs may also comprise cotton or other natural fibers. The nonwoven webs may comprise one or more layers of meltblown fibers and/or one or more layers of spunbond fibers. Some nonwoven webs may comprises a single layer of meltblown fibers and more than one layer of spunbond fibers. Some example nonwoven webs are SMS, SMMS, SSMMS, SMMSS, SMSS, or SSMS webs. The nonwoven webs of the present disclosure may also be coform webs. Coformed webs typically comprise a matrix of meltblown fibers mixed with at least one additional fibrous organic materials, such as fluff pulp, cotton, and/or rayon, for example. The coform webs may be further structured by embossing or laying down the composite on a structured belt during a coforming process. In an instance, continuous spunbond filaments are used in producing the nonwoven webs if the nonwoven webs are being made on a structured forming belt (as described below). The nonwoven webs may comprise continuous mono-component polymeric filaments comprising a primary polymeric component. The nonwoven webs may comprise continuous multicomponent polymeric filaments comprising a primary polymeric component and a secondary polymeric component. The filaments may be continuous bicomponent filaments comprising a primary polymeric component A and a secondary polymeric component B. The bicomponent filaments have a cross-section, a length, and a peripheral surface. The components A and B may be arranged in substantially distinct zones across the cross-section of the bicomponent filaments and may extend continuously along the length of the bicomponent filaments. The secondary component B constitutes at least a portion of the peripheral surface of the bicomponent filaments continuously along the length of the bicomponent filaments. The polymeric components A and B may be melt spun into multicomponent fibers on conventional melt spinning equipment. The equipment may be chosen based on the desired configuration of the multicomponent. Commercially available melt spinning equipment is available from Hills, Inc. located in Melbourne, Florida. The temperature for spinning is in the range of about 180° C. to about 230° C. The bicomponent spunbond filaments may have an average diameter from about 6 microns to about 40 microns or from about 12 microns to about 40 microns, for example.

Figure 14:
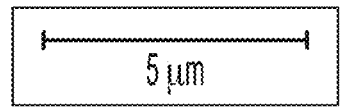
FIG. 14 is a perspective view photograph of a tri-lobal, bicomponent fiber.

The components A and B may be arranged in either a side-by-side arrangement as shown in FIG. 13A or an eccentric sheath/core arrangement as shown in FIG. 13B to obtain filaments which exhibit a natural helical crimp. Alternatively, the components A and B may be arranged in a concentric sheath/core arrangement as shown in FIG. 13C. Additionally, the component A and B may be arranged in multi-lobal sheath/core arrangement as shown in FIG. 14. Other multicomponent fibers may be produced by using the compositions and methods of the present disclosure. The bicomponent and multicomponent fibers may be segmented pie, ribbon, islands-in-the-sea configurations, or any combination thereof. The sheath may be continuous or non-continuous around the core. The fibers of the present disclosure may have different geometries that comprise round, elliptical, star shaped, rectangular, and other various geometries. Methods for extruding multicomponent polymeric filaments into such arrangements are generally known to those of ordinary skill in the art.

A wide variety of polymers are suitable to practice the present disclosure including polyolefins (such as polyethylene, polypropylene and polybutylene), polyesters, polyamides, polyurethanes, elastomeric materials and the like. Non-limiting examples of polymer materials that can be spun into filaments include natural polymers, such as starch, starch derivatives, cellulose and cellulose derivatives, hemicellulose, hemicelluloses derivatives, chitin, chitosan, polyisoprene (cis and trans), peptides, polyhydroxyalkanoates, and synthetic polymers including, but not limited to, thermoplastic polymers, such as polyesters, nylons, polyolefins such as polypropylene, polyethylene, polyvinyl alcohol and polyvinyl alcohol derivatives, sodium polyacrylate (absorbent gel material), and copolymers of polyolefins such as polyethylene-octene or polymers comprising monomeric blends of propylene and ethylene, and biodegradable or compostable thermoplastic polymers such as polylactic acid filaments, polyvinyl alcohol, filaments, and polycaprolactone filaments. In one example, thermoplastic polymer selected from the group of: polypropylene, polyethylene, polyester, polylactic acid, polyhydroxyalkanoate, polyvinyl alcohol, polycaprolactone, styrene-butadiene-styrene block copolymer, styrene-isoprene-styrene block copolymer, polyurethane, and mixtures thereof. In another example, the thermoplastic polymer is selected from the group consisting of: polypropylene, polyethylene, polyester, polylactic acid, polyhydroxyalkanoate, polyvinyl alcohol, polycaprolactone, and mixtures thereof. Alternatively, the polymer can comprise one derived from monomers which are bio-based such as bio-polyethylene, bio-polypropylene, bio-PET, or PLA, for example.

Primary component A and secondary component B may be selected so that the resulting bicomponent filament provides improved nonwoven bonding and softness. Primary polymer component A may have melting temperature which is lower than the melting temperature of secondary polymer component B.

Primary polymer component A may comprise polyethylene, polypropylene or random copolymer of propylene and ethylene. Secondary polymer component B may comprise polypropylene or random copolymer of propylene and ethylene. Polyethylenes may comprise linear low density polyethylene and high density polyethylene. In addition, secondary polymer component B may comprise polymers, additives for enhancing the natural helical crimp of the filaments, lowering the bonding temperature of the filaments, and enhancing the abrasion resistance, strength and softness of the resulting fabric.

Inorganic fillers, such as the oxides of magnesium, aluminum, silicon, and titanium, for example, may be added as inexpensive fillers or processing aides. Pigments and/or color melt additives may also be added.

The fibers of the nonwoven webs disclosed herein may comprise a slip additive in an amount sufficient to impart the desired haptics to the fiber. As used herein. "slip additive" or "slip agent" means an external lubricant. The slip agent when melt-blended with the resin gradually exudes or migrates to the surface during cooling or after fabrication, hence forming a uniform, invisibly thin coating, thereby yielding permanent lubricating effects. The slip agent may be a fast bloom slip agent.

During the making or in a post-treatment or even in both, the nonwoven webs of the present disclosure may be treated with surfactants or other agents to either hydrophilize the web or make it hydrophobic. For example, a nonwoven web used as a topsheet may be treated with a hydrophilizing material or surfactant so as to make it permeable to body exudates, such as urine and menses. For other absorbent articles, the nonwoven webs may remain in their naturally hydrophobic state or made even more hydrophobic through the addition of a hydrophobizing material or surfactant.

Suitable materials for preparing the multicomponent filaments of the nonwoven webs of the present disclosure may comprise PP3155 polypropylene obtained from Exxon Mobil Corporation and PP3854 polypropylene obtained from Exxon Mobil Corporation.

Structured Forming Belts and Process for Producing Nonwoven Webs

As mentioned above, the nonwoven webs of the present disclosure may be produced by embossing, hydroentangling, or by using a structured forming belt for fiber or filament laydown. The structured forming belt and the process of manufacture will be described now in more detail than above. The nonwoven webs may be formed directly on the structured forming belt with continuous spunbond filaments in a single forming process. The nonwoven webs may assume a shape and texture which corresponds to the shape and texture of the structured forming belt.

The present disclosure may utilize the process of melt spinning. Melt spinning may occur from about 150° C. to about 280° or from about 190° to about 230°, for example. Fiber spinning speeds may be greater than 100 meters/minute, from about 1,000 to about 10,000 meters/minute, from about 2,000 to about 7,000 meters/minute, or from about 2,500 to about 5.000 meters/minute, for example. Spinning speeds may affect the brittleness of the spun fiber, and, in general, the higher the spinning speed, the less brittle the fiber. Continuous fibers may be produced through spunbond methods or meltblowing processes.

Figure 15:
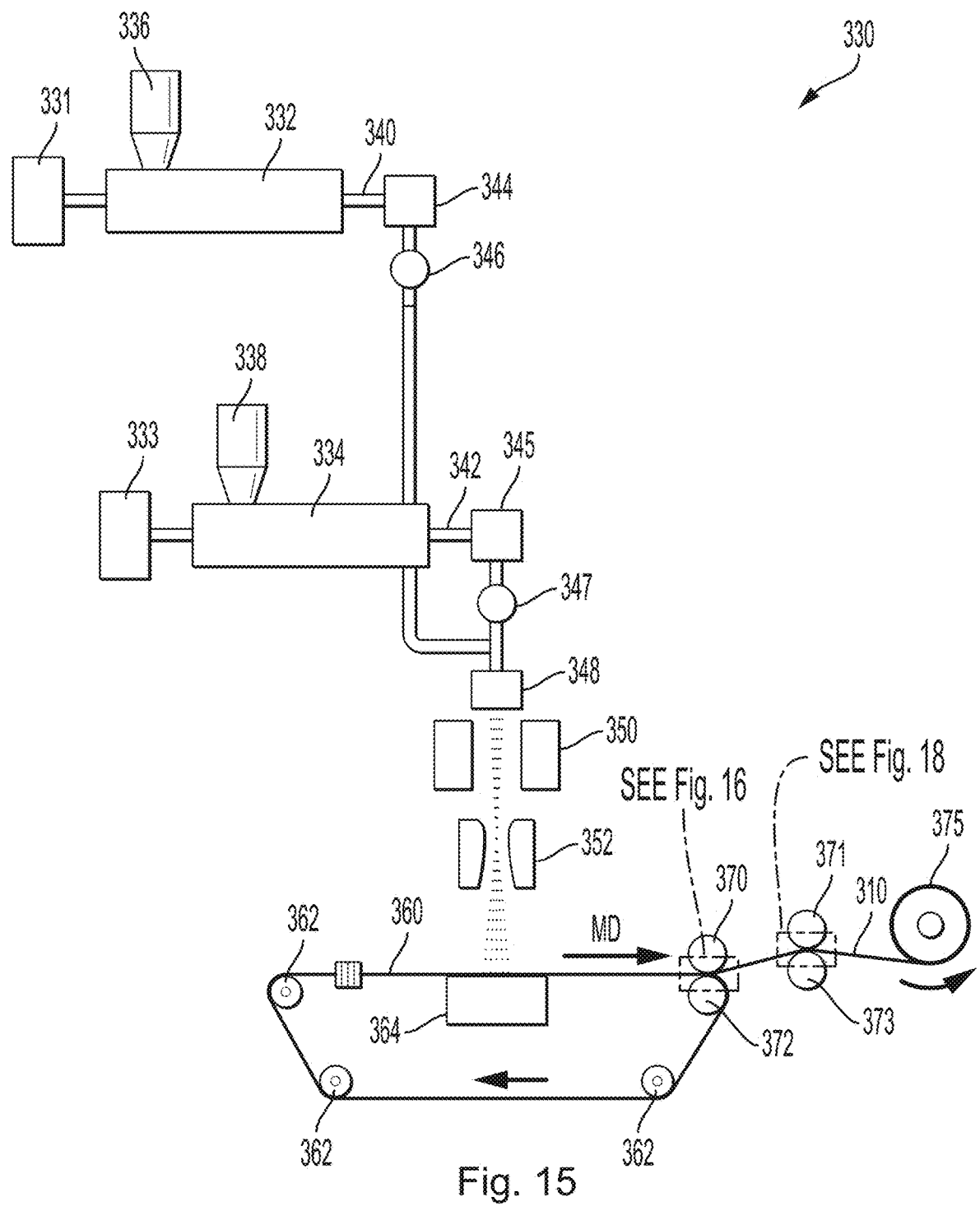
FIG. 15 is a schematic representation of an example apparatus for making the nonwoven webs of the present disclosure.

Referring to FIG. 15, a representative process line 330 for manufacturing some example nonwoven webs made on a structured forming belt of the present disclosure is illustrated. The process line 330 is arranged to produce a nonwoven web of bicomponent continuous filaments, but it should be understood that the present disclosure comprehends nonwoven webs made with monocomponent or multicomponent filaments having more than two components. The bicomponent filaments may or may not be trilobal.

The process line 330 may comprise a pair of extruders 332 and 334 driven by extruder drives 331 and 333, respectively, for separately extruding the primary polymer component A and the secondary polymer component B. Polymer component A may be fed into the respective extruder 332 from a first hopper 336 and polymer component B may be fed into the respective extruder 334 from a second hopper 338. Polymer components A and B may be fed from the extruders 332 and 334 through respective polymer conduits 340 and 342 to filters 344 and 345 and melt pumps 346 and 347, which pump the polymer into a spin pack 348. Spinnerets for extruding bicomponent filaments are generally known to those of ordinary skill in the art.

Generally described, the spin pack 348 comprises a housing which comprises a plurality of plates stacked one on top of the other with a pattern of openings arranged to create flow paths for directing polymer components A and B separately through the spinneret. The spin pack 348 has openings arranged in one or more rows. The spinneret openings form a downwardly extending curtain of filaments when the polymers are extruded through the spinneret. For the purposes of the present disclosure, spinnerets may be arranged to form side-by-side, eccentric sheath/core, or sheath/core bicomponent filaments as illustrated in FIGS. 13A-13C, as well as non-round fibers, such as tri-lobal fibers as shown in FIG. 14. Moreover, the fibers may be monocomponent having one polymeric component, such as polypropylene, for example.

The process line 330 may comprises a quench blower 350 positioned adjacent to the curtain of filaments extending from the spinneret. Air from the quench air blower 350 may quench the filaments extending from the spinneret. The quench air may be directed from one side of the filament curtain or both sides of the filament curtain.

An attenuator 352 may be positioned below the spinneret and receives the quenched filaments. Fiber draw units or aspirators for use as attenuators in melt spinning polymers are generally known to those of skill in the art. Suitable fiber draw units for use in the process of forming the nonwoven webs of the present disclosure may comprise a linear fiber attenuator of the type shown in U.S. Pat. No. 3,802,817 and eductive guns of the type shown in U.S. Pat. Nos. 3,692,618 and 3,423,266.

Generally described, the attenuator 352 may comprise an elongate vertical passage through which the filaments are drawn by aspirating air entering from the sides of the passage and flowing downwardly through the passage. A structured, endless, at least partially foraminous, forming belt 360 may be positioned below the attenuator 352 and may receive the continuous filaments from the outlet opening of the attenuator 352. The forming belt 360 may travel around guide rollers 362. A vacuum 364 positioned below the structured forming belt 360 where the filaments are deposited draws the filaments against the forming surface. Although the forming belt 360 is shown as a belt in FIG. 15, it should be understood that the forming belt may also be in other forms such as a drum. Details of particular shaped forming belts are explained below.

In operation of the process line 330, the hoppers 336 and 338 are filled with the respective polymer components A and B. Polymer components A and B are melted and extruded by the respective extruders 332 and 334 through polymer conduits 340 and 342 and the spin pack 348. Although the temperatures of the molten polymers vary depending on the polymers used, when polyethylenes are used as primary component A and secondary component B respectively, the temperatures of the polymers may range from about 190° C. to about 240° C., for example.

As the extruded filaments extend below the spinneret, a stream of air from the quench blower 350 at least partially quench the filaments, and, for certain filaments, to induce crystallization of molten filaments. The quench air may flow in a direction substantially perpendicular to the length of the filaments at a temperature of about 0° C. to about 35° C. and a velocity from about 100 to about 400 feet per minute. The filaments may be quenched sufficiently before being collected on the forming belt 360 so that the filaments may be arranged by the forced air passing through the filaments and the forming belt 360. Quenching the filaments reduces the tackiness of the filaments so that the filaments do not adhere to one another too tightly before being bonded and may be moved or arranged on the forming belt 360 during collection of the filaments on the forming belt 360 and formation of the nonwoven web.

After quenching, the filaments are drawn into the vertical passage of the attenuator 352 by a flow of the fiber draw unit. The attenuator may be positioned 30 to 60 inches below the bottom of the spinneret.

The filaments may be deposited through the outlet opening of the attenuator 352 onto the shaped, traveling forming belt 360. As the filaments are contacting the forming surface of the forming belt 360, the vacuum 364 draws the air and filaments against the forming belt 360 to form a nonwoven web of continuous filaments which assumes a shape corresponding to the shape of the structured forming surface of the structured forming belt 360. As discussed above, because the filaments are quenched, the filaments are not too tacky and the vacuum may move or arrange the filaments on the forming belt 360 as the filaments are being collected on the forming belt 330 and formed into nonwoven webs.

The process line 330 may comprise one or more bonding devices such as the cylinder-shaped compaction rolls 370 and 372, which form a nip through which the nonwoven web may be compacted (e.g., calendared) and which may be heated to bond fibers as well. One or both of compaction rolls 370, 372 may be heated to provide enhanced properties and benefits to the nonwoven webs by bonding portions of the nonwoven webs. For example, it is believed that heating sufficient to provide thermal bonding improves the nonwoven web's tensile properties. The compaction rolls may be pair of smooth surface stainless steel rolls with independent heating controllers. The compaction rolls may be heated by electric elements or hot oil circulation. The gap between the compaction rolls may be hydraulically controlled to impose desired pressure on the nonwoven web as it passes through the compaction rolls on the forming belt. As an example, with a forming belt caliper of 1.4 mm, and a spunbond nonwoven web having a basis weight of 25 gsm, the nip gap between the compaction rolls 370 and 372 may be about 1.4 mm.

Figure 16:
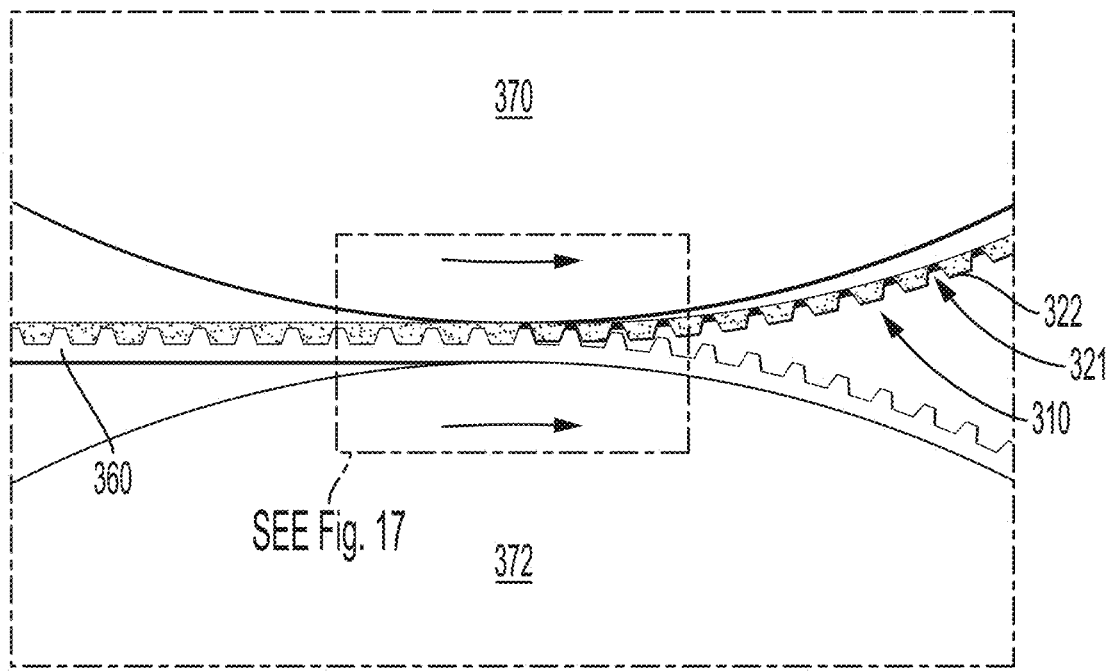
FIG. 16 is a detail of a portion of the apparatus of FIG. 15 for bonding a portion of the nonwoven webs of the present disclosure.
Figure 17:
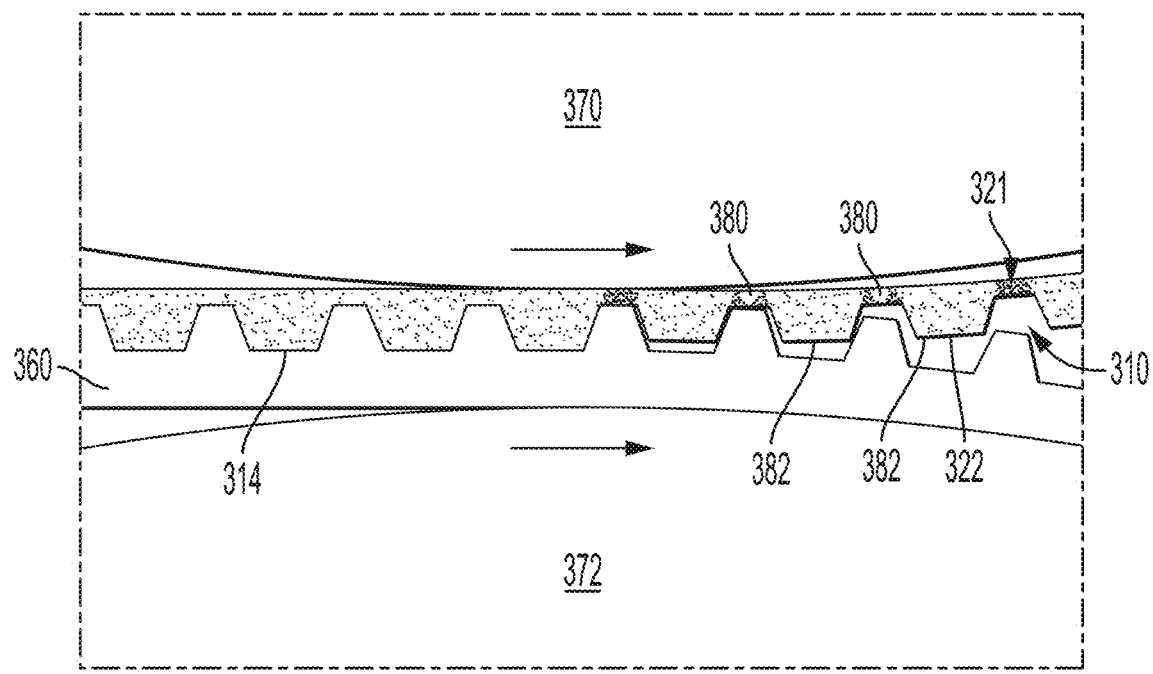
FIG. 17 is a further detail of a portion of the apparatus for bonding a portion of the nonwoven webs of the present disclosure, taken from detail FIG. 17 in FIG. 16.

An upper compaction roll 370 may be heated sufficiently to consolidate or melt fibers on a first surface of a nonwoven web 310, to impart strength to the nonwoven web so that it may be removed from forming belt 360 without losing integrity. As shown in FIGS. 16 and 17, for example, as rolls 370 and 372 rotate in the direction indicated by the arrows, the forming belt 360 with the spunbond web laid down on it enter the nip formed by rolls 370 and 372. Heated roll 370 may heat the portions of the nonwoven web 310 that are pressed against it by the raised resin elements of belt 360, i.e., in regions 321, to create bonded fibers 380 on at least the first surface of the nonwoven web 310. As can be understood by the description herein, the bonded regions so formed may take the pattern of the raised elements of forming belt 360. By adjusting temperature and dwell time, the bonding may be limited primarily to fibers closest to the first surface of the nonwoven web 310, or thermal bonding may be achieved to a second surface. Bonding may also be a discontinuous network, for example, as point bonds 390, discussed below.

The raised elements of the forming belt 360 may be selected to establish various network characteristics of the forming belt and the bonded regions of the nonwoven web 310. The network corresponds to resin making up the raised elements of the forming belt 360 and may comprise substantially continuous, substantially semi-continuous, discontinuous, or combinations thereof options. These networks may be descriptive of the raised elements of the forming belt 360 as it pertains to their appearance or make-up in the X-Y planes of the forming belt 360 or the three-dimensional features of the nonwoven webs 310.

Figure 18:
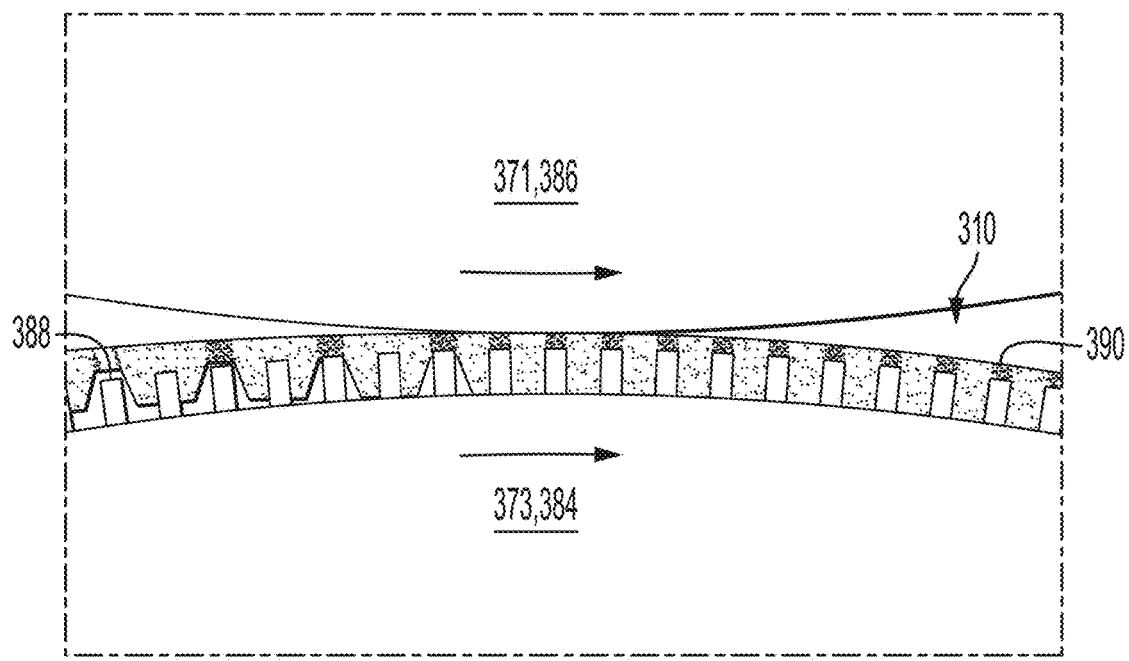
FIG. 18 is a detail of a portion of the apparatus for optional additional bonding of a portion of the nonwoven webs of the present disclosure.
Figure 19:
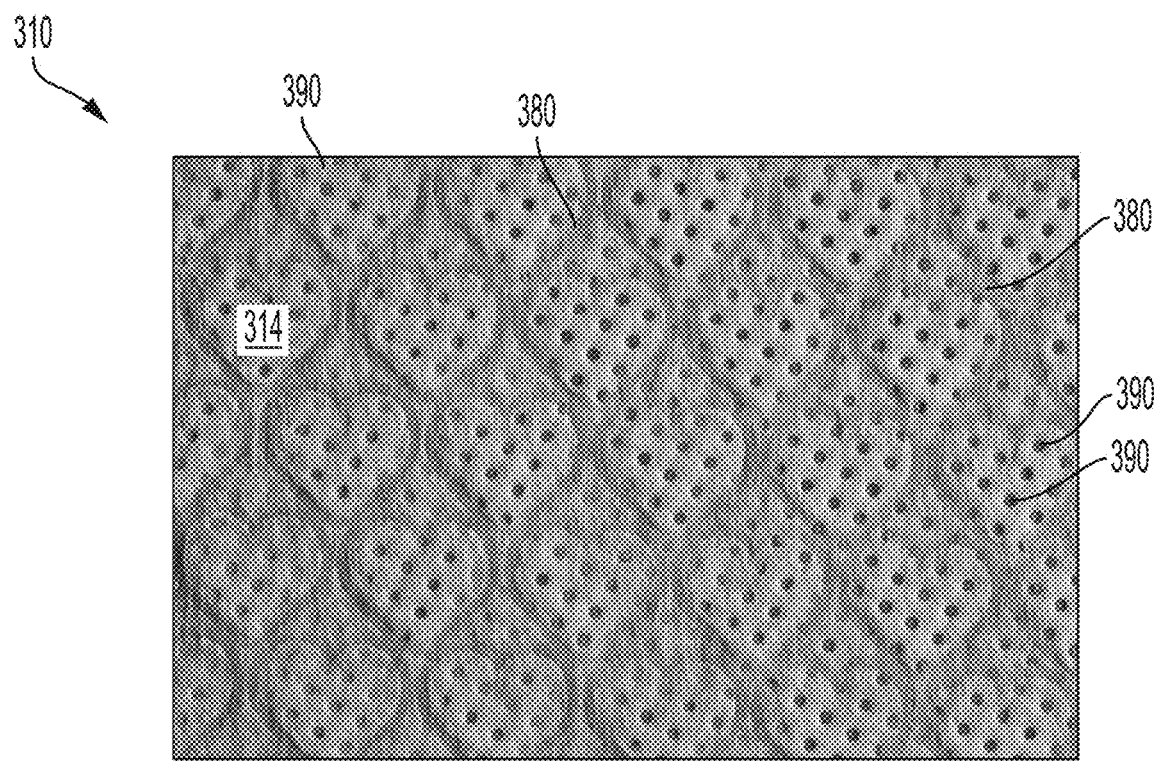
FIG. 19 is a photograph of an example nonwoven web with a different design than the nonwoven webs of the present disclosure.

After compaction, the nonwoven web 310 may leave the forming belt 360 and be calendared through a nip formed by calendar rolls 371, 373, after which the nonwoven web 310 may be wound onto a reel 375 or conveyed directly into a manufacturing operation for products, such as absorbent articles. As shown in the schematic cross-section of FIG. 18, the calendar rolls 371, 373 may be stainless steel rolls having an engraved pattern roll 384 and a smooth roll 386. The engraved roll may have raised portions 388 that may provide for additional compaction and bonding to the nonwoven web 310. Raised portions 388 may be a regular pattern of relatively small spaced apart "pins" that form a pattern of relatively small point bonds 390 in the nip of calendar rolls 371 and 373. The percent of point bonds in the nonwoven web 10 may be from about 3% to about 30% or from about 7% to about 20%, for example. The engraved pattern may be a plurality of closely spaced, regular, generally cylindrically-shaped, generally flat-topped pin shapes, with pin heights being in a range of about 0.5 mm to about 5 mm or from about 1 mm to about 3 mm, for example. Pin bonding calendar rolls may form closely spaced, regular point bonds 390 in the nonwoven web 10, as shown in an example in FIG. 19. Further bonding may be by hot-air-through bonding, for example. FIG. 19 shows a hearts pattern made by the same structured forming belt technology that may be used to make the nonwoven webs of the present disclosure.

"Point bonding", as used herein, is a method of thermally bonding a nonwoven web. This method comprises passing a web through a nip between two rolls comprising a heated male patterned or engraved metal roll and a smooth or patterned metal roll. The male patterned roll may have a plurality of raised, generally cylindrical-shaped pins that produce circular point bonds. The smooth roll may or may not be heated, depending on the application. In a nonwoven manufacturing line, the nonwoven web, which could be a non-bonded nonwoven web, is fed into the calendar nip and the fiber temperature is raised to the point for fibers to thermally fuse with each other at the tips of engraved points and against the smooth roll. The heating time is typically in the order of milliseconds. The nonwoven web properties are dependent on process settings such as roll temperatures, web line speeds, and nip pressures, all of which may be determined by the skilled person for the desired level of point bonding. Other types of point bonding known generally as hot calendar bonding may use different geometries for the bonds (other than circular shaped), such as oval, lines, circles, for example. In an example, the point bonding produces a pattern of point bonds being 0.5 mm diameter circles with 10% overall bonding area. Other bonding shapes may have raised pins having a longest dimension across the bonding surface of a pin of from about 0.1 mm to 2.0 mm and the overall bonding area ranges from about 5% to about 30%, for example.

As shown in FIG. 19, a heated compaction roll 370 may form a bond pattern, which may be a substantially continuous network bond pattern 380 (e.g., interconnected heart shaped bonds) on a first surface of the nonwoven web 310 (not shown in FIG. 19, as it faces away from the viewer), and the engraved calendar roll 373 may form relatively small point bonds 390 on a second surface 314 of the nonwoven web. The point bonds 390 may secure loose fibers that would otherwise be prone to fuzzing or pilling during use of the nonwoven web 310. The advantage of the resulting structure of the nonwoven web 310 is most evident when used as a topsheet or outer cover nonwoven material in an absorbent article, such as a diaper, for example. In use, in an absorbent article, a first surface of the nonwoven web 310 may be relatively flat (relative to second surface 14) and have a relatively large amount of bonding due to the heated compaction roll forming bonds 380 at the areas of the nonwoven web pressed by the raised elements of the forming belt 360. This bonding gives the nonwoven web 310 structural integrity, but still may be relatively stiff or rough to the skin of a user. Therefore, a first surface of the nonwoven web 310 may be oriented in a diaper or sanitary napkin to face the interior of the article, i.e., away from the body of the wearer or garment-facing. Likewise, the second surface 314 may be wearer-facing in use, and in contact with the body. The relatively small point bonds 390 may be less likely to be perceived visually or tacitly by the user, and the relatively soft three-dimensional features may remain visually free of fuzzing and pilling while feeling soft to the body in use. Further bonding may be used instead of, or in addition to, the above-mentioned bonding. Through-air bonding may also be used.

The forming belt 360 may be made according to the methods and processes described in U.S. Pat. No. 6,610,173, issued to Lindsay et al., on Aug. 26, 2003, or U.S. Pat. No. 5,514,523, issued to Trokhan et al., on May 7, 1996, or U.S. Pat. No. 6,398,910, issued to Burazin et al., on Jun. 4, 2002, or U.S. Pat. No. 8,940,376, issued to Stage et al., on Jan. 27, 2015, each with the improved features and patterns disclosed herein for making spunbond nonwoven webs. The Lindsay, Trokhan. Burazin, and Stage disclosures describe structured forming belts that are representative of papermaking belts made with cured resin on a woven reinforcing member, which belts, with improvements, may be utilized to form the nonwoven webs of the present disclosure as described herein.

Figure 20:
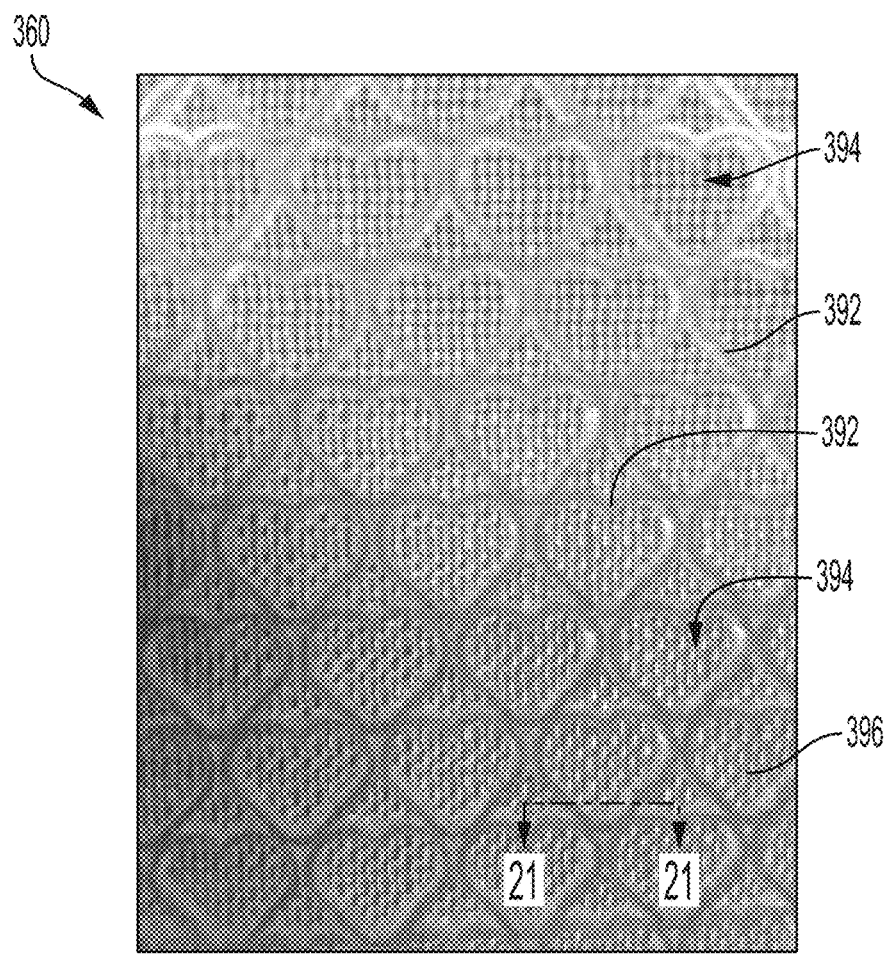
FIG. 20 is a photograph of a portion of a forming belt with the different design for forming nonwoven webs.

An example of a structured forming belt 360, and which may be made according to the disclosure of U.S. Pat. No. 5,514,523, is shown in FIG. 20. As taught therein, a reinforcing member 394 (such as a woven belt of filaments 396) is thoroughly coated with a liquid photosensitive polymeric resin to a preselected thickness. A film or negative mask incorporating the desired raised element pattern repeating elements (e.g., FIG. 22) is juxtaposed on the liquid photosensitive resin. The resin is then exposed to light of an appropriate wave length through the film, such as UV light for a UV-curable resin. This exposure to light causes curing of the resin in the exposed areas (i.e., white portions or non-printed portions in the mask). Uncured resin (resin under the opaque portions in the mask) is removed from the system leaving behind the cured resin forming the pattern illustrated, for example, the cured resin elements 392 shown in FIG. 20.

Figure 21:
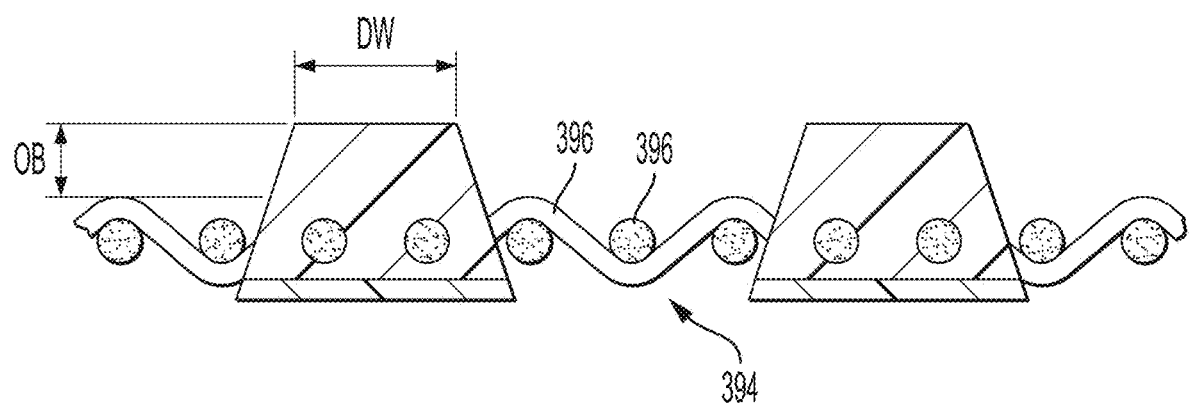
FIG. 21 is a cross-sectional depiction of a portion of the forming belt, taken about line 21-21 of FIG. 20.
Figure 22:
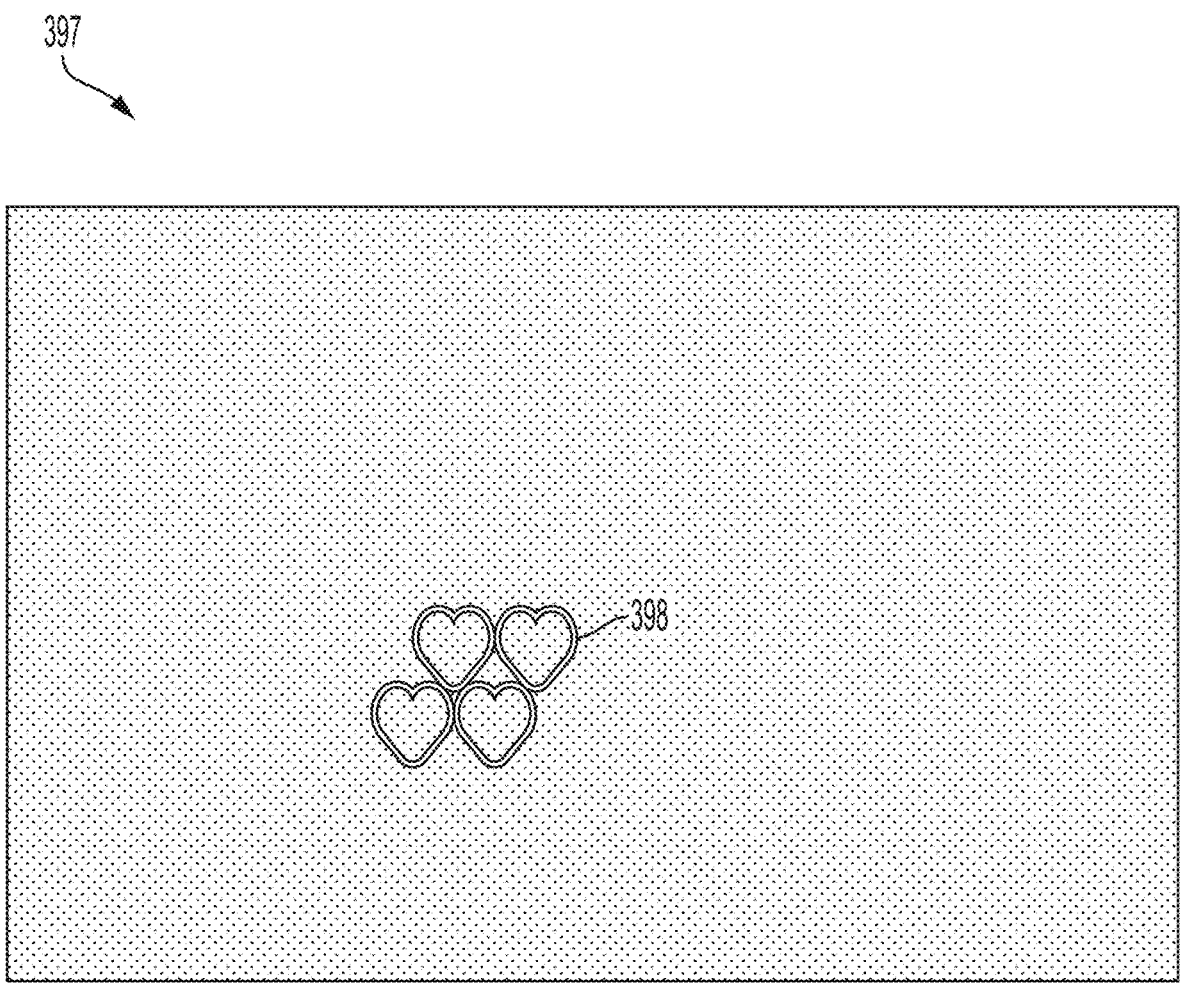
FIG. 22 is an image of a portion of a mask utilized to at least in part create the forming belt of FIG. 20.

The forming belt 360 may comprise cured resin elements 392 on a woven reinforcing member 394. The reinforcing member 394 may be made of woven filaments 396 as is generally known in the art of papermaking belts, including resin coated papermaking belts. The cured resin elements may have the general structure depicted in FIG. 20, and are made by the use of a mask 397 having the dimensions indicated in FIG. 22 As shown in schematic cross-section in FIG. 21, cured resin elements 392 flow around and are cured to "lock on" to the reinforcing member 394 and may have a width at a distal end DW of about 0.020 inches to about 0.060 inches, or from about 0.025 inches to about 0.030 inches, and a total height above the reinforcing member 394, referred to as over burden. OB, of about 0.030 inches to about 0.120 inches or about 0.50 inches to about 0.80 inches, or about 0.040 inches. FIG. 22 represents a portion of a mask 397 showing the design and representative dimensions for one repeat unit of the repeating hearts design, shown herein merely as an example. The white portion 398 is transparent to UV light, and in the process of making the belt, as described in U.S. Pat. No. 5,514,523, permits UV light to cure an underlying layer of resin which is cured to form the raised elements 392 on the reinforcing member 394. After the uncured resin is washed away, the forming belt 360 having a cured resin design as shown in FIG. 20 is produced by seaming the ends of a length of the forming belt, the length of which may be determined by the design of the apparatus, as depicted in FIG. 15.

The nonwoven webs disclosed herein may be fluid permeable. The entire nonwoven web may be considered fluid permeable or some regions may be fluid permeable. By fluid permeable, as used herein, with respect to the nonwoven web is meant that the nonwoven web has at least one region which permits liquid to pass through under in-use conditions of a consumer product or absorbent article. For example, if used as a topsheet on a disposable absorbent article, the nonwoven web may have at least one zone having a level of fluid permeability permitting urine to pass through to an underlying absorbent core. By fluid permeable, as used herein with respect to a region, it is meant that the region exhibits a porous structure that permits liquid to pass through.

Because of the nature of the structured forming belts and other apparatus elements, as described herein, the three-dimensional features of the nonwoven web have average intensive properties that may differ between first and second regions, or from feature to feature in ways that provide for beneficial properties of the nonwoven web when used in personal care articles, garments, medical products, and cleaning products. For example, a first region may have a basis weight or density that is different from the basis weight or density of a second region, and both may have a basis weight or density that is different from that of a third region, providing for beneficial aesthetic and functional properties related to fluid acquisition, distribution and/or absorption in diapers or sanitary napkins.

The average intensive property differential between the various regions of the nonwoven webs is believed to be due to the fiber distribution and compaction resulting from the apparatus and method described herein. The fiber distribution occurs during the fiber laydown process, as opposed to, for example, a post making process such as embossing processes. Because the fibers are free to move during a process such as a melt spinning process, with the movement determined by the nature of the features and air permeability of the forming belt and other processing parameters, the fibers are believed to be more stable and permanently formed in nonwoven web.

In structured forming belts having multiple zones, the air permeability in each zone may be variable such that the intensive properties of average basis weight and average volumetric density in the zones may be varied. Variable air permeabilities in the various zones causes fiber movement during laydown. The air permeability may be between about 400 to about 1000 cfm, or between about 400 to about 800 cfm, or between about 500 cfm and about 750 cfm, or between about 650 to about 700 cfm, specifically reciting all 1 cfm increments within the specified ranges and all ranges formed therein or thereby.

A structured forming belt may comprise an endless foraminous member comprising a first surface and a second surface, a curable resin extending from the first surface of the foraminous member, and a visually discernible pattern of three-dimensional features on the endless foraminous member. The three-dimensional features may comprise one or more first regions and a plurality of second regions. The one or more first regions may comprise the resin and the plurality of second regions may be free of the resin.

Bio-Based Content for Absorbent Article Components

Components of the disposable absorbent article (i.e., diaper, disposable pant, adult incontinence article, sanitary napkin, pantiliner, etc.) described in this specification may at least partially be comprised of bio-sourced content as described in U.S. Pat. Appl. Publ. No. 2007/0219521A1 Hird et al., published on Sep. 20, 2007, U.S. Pat. Appl. Publ. No. 2011/0139658A1 Hird et al., published on Jun. 16, 2011, U.S. Pat. Appl. Publ. No. 2011/0139657A1 Hird et al., published on Jun. 16, 2011, U.S. Pat. Appl. Publ. No 2011/0152812A1 Hird et al., published on Jun. 23, 2011, U.S. Pat. Appl. Publ. No. 2011/0139662A1 Hird et al., published on Jun. 16, 2011, and U.S. Pat. Appl. Publ. No. 2011/0139659A1 Hird et al., published on Jun. 16, 2011. These components include, but are not limited to, topsheet nonwovens, backsheet films, backsheet nonwovens, side panel nonwovens, barrier leg cuff nonwovens, super absorbents, nonwoven acquisition layers, core wrap nonwovens, adhesives, fastener hooks, and fastener landing zone nonwovens and film bases.

In some forms, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In a form, the disposable absorbent article component may be ground into particulates less than about 20 mesh using known grinding methods (e.g., Wiley® mill), and a representative sample of suitable mass taken from the randomly mixed particles.

Nonwoven webs may comprise multicomponent fibers or bicomponent fibers, where at least one or more of the components are bio-based. Examples include side-by-side, sheath/core, or islands in the sea configurations, where one or more or all of the components are bio-based.

Emtec

In addition to providing improved texture perception, the nonwoven webs of the present disclosure provide improved softness and texture. The present disclosure further solves the contradiction between high softness and high visible texture. Softness, texture (i.e., smoothness), and/or stiffness may be measured by an Emtec Tissue Softness Analyzer, according to the Emtec Test herein. Tactile softness is measured as TS7. Texture/Smoothness is measured as TS750. Stiffness is measured as D.

A portion of, or all of, the nonwoven webs of the present disclosure may have a TS7 value in the range of about 1 dB $V^2$ rms to about 4.5 dB $V^2$ rms, about 2 dB $V^2$ rms to about 4.5 dB $V^2$ rms, or about 2 dB $V^2$ rms to about 4.0 dB $V^2$ rms. The portion of, or all of, the nonwoven webs of the present disclosure may also have a TS750 value in the range of about 4 dB $V^2$ rms to about 30 dB $V^2$ rms, about 6 dB $V^2$ rms to about 30 dB $V^2$ rms, about 6 dB $V^2$ rms to about 20 dB $V^2$ rms, about 6 dB $V^2$ rms to about 15 dB $V^2$ rms, about 6 dB $V^2$ rms to about 12 dB $V^2$ rms, or about 6.5 dB $V^2$ rms to about 10 dB $V^2$ rms. The portion of, or all of, the wearer-facing surfaces of the topsheets of the present disclosure may also have a D value in the range of about 1 mm/N to about 10 mm/N, about 3 mm/N to about 8 mm/N, about 2 mm/N to about 6 mm/N, about 2 mm/N to about 4 mm/N, or about 3 mm/N to about 4 mm/N. All values are measured according to the Emtec Test herein. The TS7 value is tactile softness, so low numbers are desired (the lower the number, the more soft the material is). The TS750 value is texture so a high number is desired (the higher the number, the more texture the material has). Having a low TS7 value and a high texture value is contradictory in that typically the more texture a nonwoven fabric has, the less soft it is. The Applicants, without wishing to be bound by theory, have discovered the unexpected results of highly textured nonwoven fabrics that still are very soft.

Nonwoven Webs with Improved Texture and Absorbency Perception and Improved Softness As discussed herein, the nonwoven webs for absorbent articles of the present disclosure result in improved texture and absorbency perception and improved softness. The nonwoven webs for absorbent articles may comprise a first surface, a second surface, and a visually discernible pattern of three-dimensional features on the first surface and/or the second surface. The nonwoven webs may comprise continuous fibers. The three-dimensional features may comprise one or more, or a plurality of, first regions and a plurality of second regions. The one or more first regions may have a first value of an average intensive property. The plurality second regions may have a second value of the average intensive property. The first value and the second value may be different and are both greater than zero. The average intensive property may be basis weight, caliper, and/or volumetric density. The nonwoven webs may have a Single Layer Chroma value in the range of about 1.0 to about 3.5, or about 1.5 to about 3.5, according to the Delta Chroma and Single Layer Chroma Test. The nonwoven webs may have a Delta Chroma value in the range of about +0.1 to about +3.5, about +0.5 to about +3.5, about +1.0 to about +3.5, or about +1.5 to about +3.5, according to the Delta Chroma and Single Layer Chroma Test.

The nonwoven webs may comprise bonds at fiber intersections formed by passing hot air through the nonwoven webs and using a process referred to as through-air bonding. In other instances, the nonwoven webs may be hydroentangled. In other instances, the nonwoven webs may comprise calendar bonds configured to join the fibers together. In still other instances, the nonwoven webs may be formed on a structured forming belt as described herein with respect to FIGS. 15-22.

The nonwoven web of the present disclosure may comprise a second, visually discernible pattern of three-dimensional features on the first surface or the second surface. The second, visually discernible pattern of three-dimensional features may be different than the visually discernible pattern. The three-dimensional features may comprise one or more, or a plurality of, third regions and a plurality of fourth regions. The one or more third regions may be different than the plurality of fourth regions in a value of an average intensive property, such as basis weight, caliper, and/or volumetric density.

The nonwoven webs of the present disclosure may comprise multicomponent fibers, such as bicomponent fibers (see e.g., FIGS. 13A-13C). At least one component of the multicomponent fibers may be bio-based, such as PLA, bio-PE, or bio-PP, for example.

The nonwoven webs of the present disclosure may have basis weights in the range of about 10 gsm to about 100 gsm, about 15 gsm to about 50 gsm, or about 15 gsm to about 40 gsm, according to the Basis Weight Test. The nonwoven webs may be spunbond nonwoven webs.

The nonwoven webs of the present disclosure may have a TS7 value in the range of about 1 dB $V^2$ rms to about 4.5 dB $V^2$ rms, according to the Emtec Test, and a TS750 value in the range of about 6 dB $V^2$ rms to about 30 dB $V^2$ rms, according to the Emtec Test. The nonwoven webs of the present disclosure may have a D value in the range of about 2 mm/N to about 6 mm/N, according to the Emtec Test. The ranges of TS7, TS750, and D characterize the improved softness of the nonwoven webs of the present disclosure.

The nonwoven webs discussed herein may form at least portions of, or all of, one or nonwoven components of absorbent articles, such as the nonwoven components discussed above.

Nonwoven webs for absorbent articles may comprise a first surface, a second surface, a plurality of continuous spunbond fibers, and a visually discernible pattern of three-dimensional features on the first surface or the second surface. The three-dimensional features may comprise one or more, or a plurality of, first regions and a plurality of second regions. The one or more first regions may have a first value of an average intensive property. The plurality of second regions may have a second value of the average intensive property. The first value and the second value may be different. The first value and the second value are greater than zero. The average intensity property may be basis weight, volumetric density, and/or caliper. The nonwoven webs may have a Single Layer Chroma value in the range of about 1.0 to about 3.5, or about 1.5 to about 3.5, according to the Delta Chroma and Single Layer Chroma Test. The nonwoven webs may have a Delta Chroma value in the range of about +0.1 to about +3.5, about +0.5 to about +3.5, about +1.0 to about +3.5, or about +1.5 to about +3.5, according to the Delta Chroma and Single Layer Chroma Test.

Nonwoven webs for absorbent articles may comprise a first surface, a second surface, and a first visually discernible pattern of three-dimensional features on the first surface or the second surface. The nonwoven webs may comprise continuous fibers. The three-dimensional features may comprise one or more, or a plurality of, first regions and a plurality of second regions. The one or more first regions may be different than the plurality of second regions in a value of a first average intensive property. The first portion of the nonwoven web in the first visually discernible pattern may have a Single Layer Chroma value in the range of about 1.0 to about 3.5, or about 1.5 to about 3.5, according to the Delta Chroma and Single Layer Chroma Test. The first portion of the nonwoven web in the first visually discernible pattern may have a Delta Chroma value in the range of about +0.1 to about +3.5, about +0.5 to about +3.5, or about +1.0 to about +3.5, according to the Delta Chroma and Single Layer Chroma Test. The nonwoven webs may comprise a second visually discernible pattern of three-dimensional features on the first surface or the second surface. The three-dimensional features may comprise one or more, or a plurality of, third regions and a plurality of fourth regions. The one or more third regions may be different than the plurality of fourth regions in a value of a second average intensive property. The first average intensive property and the second average intensive property may be basis weight, caliper, and/or volumetric density.

Spunbond or other nonwoven webs for absorbent articles may comprise a first surface, a second surface, and a visually discernible pattern of three-dimensional features on the first surface or the second surface. The three-dimensional features may comprise one or more of, or a plurality of, first regions and a plurality of second regions. The one or more first regions may have a first value of an average intensive property. The plurality second regions may have a second value of the average intensive property. The first value and the second value may be different. The first value and the second value are greater than zero. The spunbond or other nonwoven webs may have a Single Layer Chroma value in the range of about 1.0 to about 3.5, or about 1.5 to about 3.5, according to the Delta Chroma and Single Layer Chroma Test. The spunbond or other nonwoven webs may have a Delta Chroma value in the range of about +0.1 to about +3.5, about +0.5 to about +3.5, about +1.0 to about +3.5, or about +1.5 to about +3.5, according to the Delta Chroma and Single Layer Chroma Test. A portion of, or all of, the nonwoven webs may have a TS7 value in the range of about 1 dB $V^2$ rms to about 4.5 dB $V^2$ rms, according to the Emtec Test. The portion of, or all of, the nonwoven webs may have a TS750 value in the range of about 6 dB $V^2$ rms to about 30 dB $V^2$ rms, according to the Emtec Test.

Nonwoven webs of the present disclosure may have a plurality of three-dimensional features and/or apertures. An example material with three-dimensional features and/or apertures is disclosed in U.S. Pat. No. 10,206,826, granted on Feb. 19, 2019, to Olaf Erik ISELE et al. The nonwoven webs may have a Single Layer Chroma value in the range of about 1.0 to about 3.5, or about 1.5 to about 3.5, according to the Delta Chroma and Single Layer Chroma Test. The nonwoven webs may have a Delta Chroma value in the range of about +0.1 to about +3.5, about +0.5 to about +3.5, about +1.0 to about +3.5, or about +1.5 to about +3.5, according to the Delta Chroma and Single Layer Chroma Test.

The nonwoven webs of the present disclosure may have a low level of colorant, additive, and/or dye to help with texture perception, absorbency perception, and softness perception. The low level of the colorant, additive, and/or dye may be low enough so that the nonwoven webs appear to still be "white" to the human eye. For example, if a teal colorant, additive, and/or dye is used, the resulting nonwoven material will still appear to be white to the human eye, but texture in the nonwoven web will be more enhanced when viewed. This leads to improved perceptions of absorbency and softness.

As an example, a colorant masterbatch may be used that is a solid additive that comprises pigments typically in the range of about 15% to about 65% actives with a carrier resin, such as polypropylene, polyethylene, and/or polyester. The colorant masterbatch is designed to deliver certain target color which is described as a "let-down ratio". For example, in nonwoven webs, a masterbatch at 2% let-down ratio will result in a target color when 2% of the masterbatch is blended with 98% of the corresponding nonwoven resin, such as polypropylene, polyethylene, and/or polyester, for example. A conventional let-down ratio may be in the range of about 1.5% to about 5%. This level of let-down ratio, however, causes the nonwoven webs to appear as colored to the human eye, such as teal, for example. In the present disclosure, the add-on levels of the masterbatch are significantly lower for enhancing the texture perception, absorbency perception, and softness perception, without the color being visible to the human eye (i.e., the nonwoven web still appears to be white).

An example colorant may be purchased from Ampacet Corporation located at 660 White Plans Rd. Tarrytown, NY 10591. One example colorant is blue colorant from Ampacet Corporation under the product name Ampacet 4600664-N.

Figure 23:
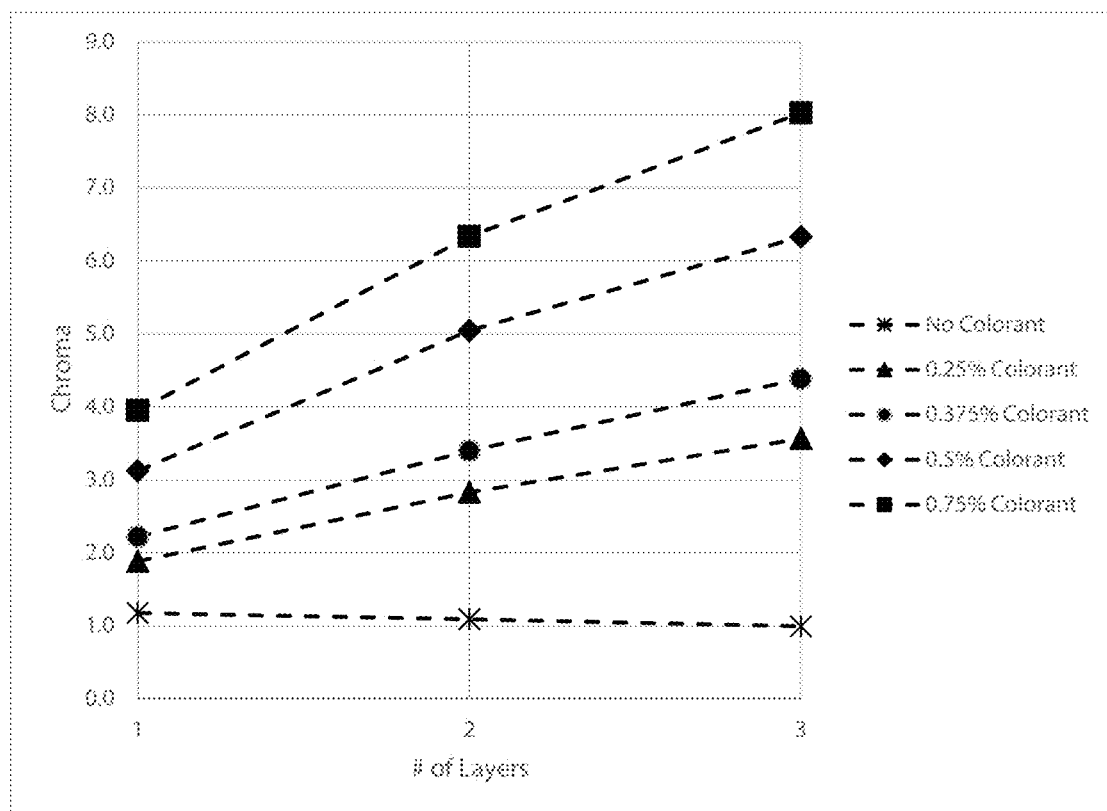
FIG. 23 is a graph of Chroma vs. number of layers of nonwoven material.

FIG. 23 is a graph of Chroma (y-axis) and number of layers of nonwoven material (x-axis). The first material had no colorant, additive, and/or dye. The colorant, additive, and/or dye in the second to fifth materials in the example of FIG. 23 was blue. The second material had 0.25%, by weight of the nonwoven composition (the melted composition used to create fibers), of the colorant, additive, or dye. The third material had 0.37%, by weight of the nonwoven composition, of the colorant, additive, and/or dye. The fourth material had 0.5%, by weight of the nonwoven composition, of the colorant, additive, and/or dye. The fifth material had 0.75%, by weight of the nonwoven composition, of the colorant, additive, and/or dye. Table 1 below shows the data that is plotted on the graph of FIG. 23. In the fourth and the fifth materials, the nonwoven webs started to appear "blue," whereas the second and third materials still appeared to be "white."

As an example, the % by weight of the nonwoven composition for a blue colorant, additive, or dye may be in the range of about 0.15% to about 0.4%, about 0.15% to about 0.375%, about 0.15% to about 0.35%, about 0.15% to about 0.325%, about 0.15% to about 0.3%, about 0.15% to about 0.275%, about 0.15% to about 0.25%, about 0.175%, about 0.2%, about 0.225%, or about 0.25%, for example, specifically reciting all 0.001 increments within the specified ranges and all ranges formed therein or thereby. Other ranges may also be suitable for different colors other than blue.

TABLE 1

| | Number of Layers (all layers 25 gsm) | Colorant, Additive, or Dye | Single Layer Chroma | Delta Chroma |
|---|---|---|---|---|
| First material | 1 | 0.0% | 1.2 | |
| First material | 2 | 0.0% | 1.1 | |
| First material | 3 | 0.0% | 1.0 | −0.2 |
| Second material | 1 | 0.25% | 1.9 | |
| Second material | 2 | 0.25% | 2.8 | |
| Second material | 3 | 0.25% | 3.6 | +1.7 |
| Third material | 1 | 0.375% | 2.2 | |
| Third material | 2 | 0.375% | 3.4 | |
| Third material | 3 | 0.375% | 4.4 | +2.2 |
| Fourth material | 1 | 0.5% | 3.1 | |
| Fourth material | 2 | 0.5% | 5.0 | |
| Fourth material | 3 | 0.5% | 6.3 | +3.2 |
| Fifth material | 1 | 0.75% | 3.9 | |
| Fifth material | 2 | 0.75% | 6.3 | |
| Fifth material | 3 | 0.75% | 8.0 | +4.1 |

The nonwoven webs of the present disclosure may have a Single Layer Chroma value in the range of about 0.5 to about 4, about 0.5 to about 3.5, about 0.75 to about 3.5, about 1.0 to about 3.5, about 1.25 to about 3.5, about 1.5 to about 3.5, about 1.75 to about 3.5, about 1.9 to about 3.9, about 1.9, about 2.2, about 3.1, or about 3.9, specifically reciting all 0.1 increments within the specified ranges and all ranges formed therein or thereby.

The nonwoven webs of the present disclosure may have a Delta Chroma value in the range of about +0.1 to about +6, about +0.25 to about +6, about +0.5 to about +6, about +1 to about +6, about +1 to about +5, about +1 to about +4.5, about +1 to about +4.1, about +0.1 to about +3.5, about +0.5 to about +3.5, about +1 to about +3.5, about +1.5 to about +3.5, about +1.0 to about +4, about +1.0 to about +4.1, about +1.7 to about +4.1, about +1.7, about +2.2, about +3.2, or about +4.1, specifically reciting all 0.1 increments within the specified ranges and all ranges formed therein or thereby.

Figure 24:
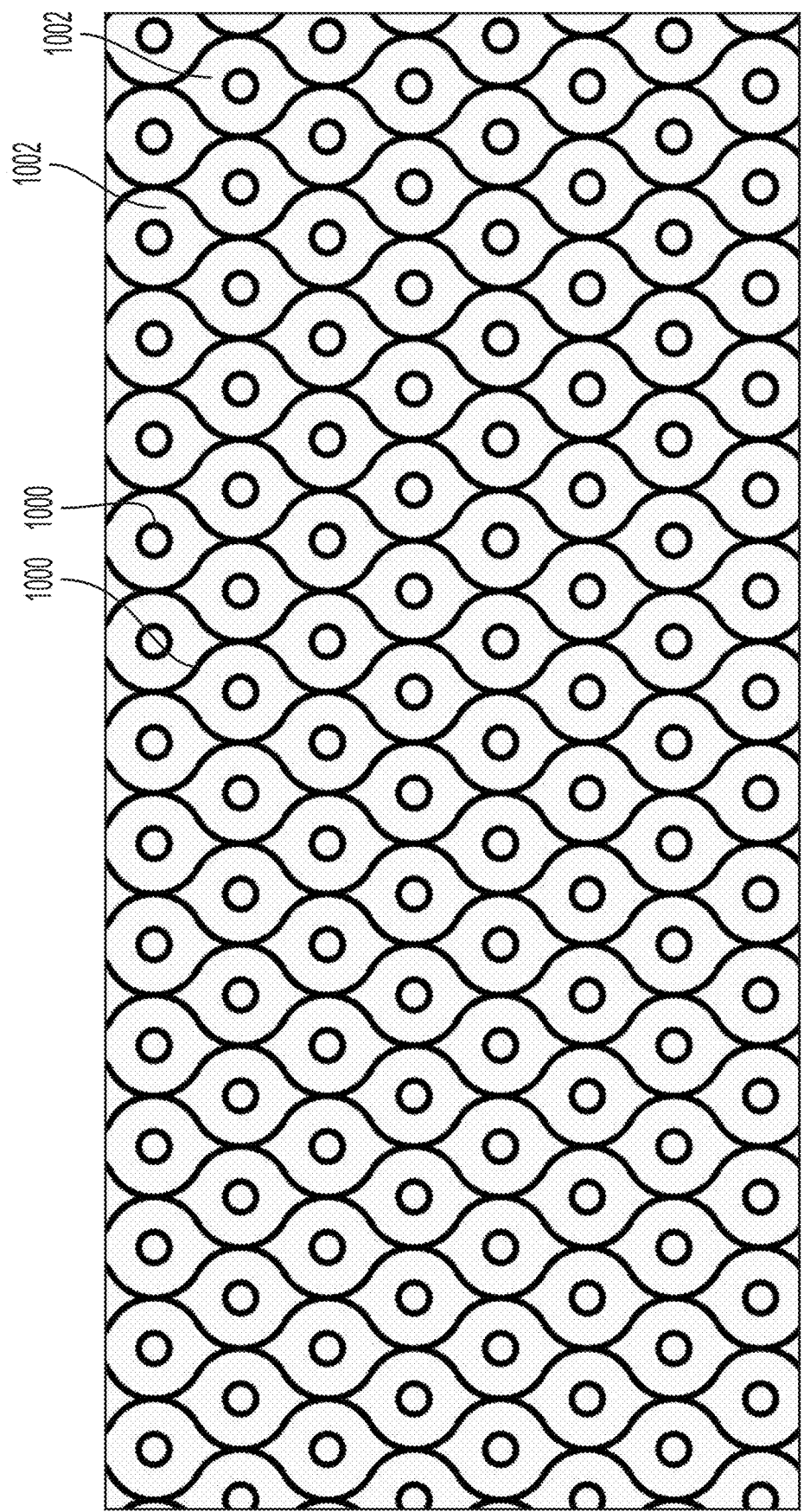
FIG. 24 is an example of a visually discernible pattern of three-dimensional features for a nonwoven web.

An example visually discernible pattern of three-dimensional features for a nonwoven web of the present disclosure is illustrated in FIG. 24. The three-dimensional features comprise a plurality of first regions 1000 and a plurality of second regions 1002.

Test Methods

Air Permeability Test Method

The Air Permeability Test is used to determine the level of air flow in cubic feet per minute (cfm) through a forming belt. The Air Permeability Test is performed on a Texas Instruments model FX3360 Portair Air Permeability Tester, available from Textest AG, Sonnenbergstrasse 72, CH 8603 Schwerzenbach, Switzerland. The unit utilizes a 20.7 mm orifice plate for air permeability ranges between 300-1000 cfm. If air permeability is lower than 300 cfm the orifice plate needs to be reduced; if higher than 1000 cfm the orifice plate needs to be increased. Air permeability can be measured in localized zones of a forming belt to determine differences in air permeability across a forming belt.

Test Procedure

1. Power on the FX3360 instrument.
2. Select a pre-determined style having the following setup:
    a. Material: Standard
    b. Measurement Property: Air Permeability (AP)
    c. Test Pressure: 125 Pa (pascals)
    d. T-factor: 1.00
    e. Test point pitch: 0.8 inch.
3. Position the 20.7 mm orifice plate on the top side of the forming belt (the side with the three-dimensional protrusions) at the position of interest.
4. Selecting "Spot Measurement" on the touch screen of the testing unit.
5. Reset the sensor prior to measurement, if necessary.
6. Once reset, select the "Start" button to begin measurement.
7. Wait until the measurement stabilizes and record the cfm reading on the screen.
8. Select the "Start" button again to stop measurement.

Basis Weight Test

Basis weight of the nonwoven webs described herein may be determined by several available techniques, but a simple representative technique involves taking an absorbent article or other consumer product, removing any elastic which may be present and stretching the absorbent article or other consumer product to its full length. A punch die having an area of 45.6 cm² is then used to cut a piece of the nonwoven web (e.g., topsheet, outer cover) from the approximate center of the absorbent article or other consumer product in a location which avoids to the greatest extent possible any adhesive which may be used to fasten the nonwoven web to any other layers which may be present and removing the nonwoven web from other layers (using cryogenic spray, such as Cyto-Freeze, Control Company, Houston, Texas, if needed). The sample is then weighed and dividing by the area of the punch die yields the basis weight of the nonwoven web. Results are reported as a mean of 5 samples to the nearest 0.1 gram per square meter (gsm).

Delta Chroma and Single Layer Chroma Test

The Delta Chroma and Single Layer Chroma values are an indication of the presence and intensity of color in a layer of material. Generally, Chroma is calculated from the reflectance measurements of the CIE 1976 L*a*b* color values. Chroma is measured using a spectrophotometer with a computer interface (a suitable instrument is the HunterLab LabScan XE running Universal Software, as available from Hunter Associates Laboratory Inc., Reston, VA). All testing is performed in a conditioned room maintained at about 23 t 2° C. and about 50 t 2% relative humidity.

To obtain a sample, tape an absorbent article to a rigid flat surface in a planar configuration with the layer of material for testing facing upward. Any elastics may be cut to facilitate laying the article flat. Using a razor blade, excise the sample layer material from the underlying layers of the article. The sample layer material is carefully removed such that its longitudinal and lateral extension is maintained to avoid distortion. A cryogenic spray (such as Cyto-Freeze, Control Company, Houston TX) can be used to remove the specimen from the underlying layers if necessary. Three replicate layers of material obtained from three substantially similar articles are prepared for analysis. A layer of raw material is prepared for testing by extending it under the same process conditions, and to the same extent, as it would be for use on the absorbent article. Precondition the samples at about 23° C.±2 C.° and about 50%±2% relative humidity for 2 hours prior to testing.

Standardize the instrument using the 2.00 inch port size (indicate the 1.75 inch area view to the software) utilizing the manufacturer supplied black tile, then white tile. Calibrate the instrument according to manufacturer's specifications using their supplied standard tiles. Configure the software to measure color using the CIE 1976 L*a*b* color scale, D65 illuminant and 10° standard observer.

Place a single layer sample over the measurement port. Gently pull the sample taut, without stretching, to ensure that it does not pillow into the port, and then back it with the standard white tile. Make sure that the area of the sample to be measured faces the port and completely covers the port. Take a reading and record the individual L*, a*, and b* values, then remove the white tile and add a second layer of material on top of the first layer and back them with the white tile. Obtain and record a second reading, and then in like manner add a third layer of material on top of the first two layers, obtain and record a third reading. Calculate the Chroma values for each of the three material layer readings according to the following equation:

$$\text{Chroma} = \sqrt{a^{*2} + b^{*2}}$$

The Chroma value for the single layer of material is recorded as the Single Layer Chroma value to the nearest 0.1 units. The Delta Chroma value is then calculated by subtracting the Chroma value obtained from a single layer of material from the Chroma value obtained from the three layers of material. Record the Delta Chroma value to the nearest 0.1 units, indicating if it is positive or negative value. Repeat this test on five substantially similar sets of samples and record the individual results. Calculate and report the average Single Layer Chroma value, and the average Delta Chroma value to the nearest 0.1 units.

Emtec Test

The Emtec Test is performed on portions of nonwoven webs of interest. In this test, TS7, TS750, and D values are measured using an Emtec Tissue Softness Analyzer ("Emtec TSA") (Emtec Electronic GmbH, Leipzig, Germany) interfaced with a computer running Emtec TSA software (version 3.19 or equivalent). The Emtec TSA includes a rotor with vertical blades which rotate on the test sample at a defined and calibrated rotational speed (set by manufacturer) and contact force of 100 mN. Contact between the vertical blades and the test sample creates vibrations both in the blades and in the test piece, and the resulting sound is recorded by a microphone within the instrument. The recorded sound file is then analyzed by the Emtec TSA software to determine TS7 and TS750 values. The D value is a measure of sample stiffness and is based on the vertical distance required for the contact force of the blades on test sample to be increased from 100 mN to 600 mN. The sample preparation, instrument operation, and testing procedures are performed according the instrument manufacturer's specifications.

Sample Preparation

A test sample is prepared by cutting a square or circular portion of interest from a nonwoven web of an absorbent article. It is preferable that freeze spray is not used to remove the nonwoven web to be analyzed from the absorbent article, though it is acceptable to use freeze spray in a distal region to aid in initiating the separation of layers. Test samples are cut to a length and width (diameter in the case of a circular sample) of no less than about 90 mm and no greater than about 120 mm to ensure the sample can be clamped into the TSA instrument properly. (If an absorbent article does not contain a sufficiently large area of the substrate of interest to extract a sample of the size specified above, it is acceptable to sample equivalent material from roll stock.) Test samples are selected to avoid unusually large creases or folds within the testing region. Six substantially similar replicate samples are prepared for testing.

All samples are equilibrated at TAPPI standard temperature and relative humidity conditions (23° C.±2 C.° and 50%±2%) for at least 2 hours prior to conducting the TSA testing, which is also conducted under TAPPI conditions.

Testing Procedure

The instrument is calibrated according to the Emtec's instructions using the 1-point calibration method with the appropriate reference standards (so-called "ref. 2 samples," or equivalent, available from Emtec).

A test sample is mounted in the instrument with the surface of interest facing upward, and the test is performed according to the manufacturer's instructions. The software displays values for TS7, TS750, and D when the automated instrument testing routine is complete. TS7 and TS750 are each recorded to the nearest 0.01 dB $V^2$ rms, and D is recorded to the nearest 0.01 mm/N. The test sample is then removed from the instrument and discarded. This testing procedure is performed individually on the corresponding surfaces of interest of each of the six of the replicate samples (wearer-facing surface for topsheet samples and garment-facing surface for outer cover nonwoven material samples).

The value of TS7, TS750, and D are each averaged (arithmetic mean) across the six sample replicates. The average values of TS7 and TS750 are reported to the nearest 0.01 dB $V^2$ rms. The average value of D is reported to the nearest 0.01 mm/N.

Micro-CT Intensive Property Measurement Method

The micro-CT intensive property measurement method measures the basis weight, thickness and volumetric density values within visually discernable regions of a substrate sample. It is based on analysis of a 3D x-ray sample image obtained on a micro-CT instrument (a suitable instrument is the Scanco pCT 50 available from Scanco Medical AG. Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and save the raw data. The 3D image is then analyzed using image analysis software (a suitable image analysis software is MATLAB available from The Mathworks, Inc., Natick, MA, or equivalent) to measure the basis weight, thickness and volumetric density intensive properties of regions within the sample.

Sample Preparation:

To obtain a sample for measurement, lay a single layer of the dry substrate material out flat and die cut a circular piece with a diameter of 30 mm.

If the substrate material is a layer of an absorbent article, for example a topsheet, backsheet nonwoven, acquisition layer, distribution layer, or other component layer; tape the absorbent article to a rigid flat surface in a planar configuration. Carefully separate the individual substrate layer from the absorbent article. A scalpel and/or cryogenic spray (such as Cyto-Freeze. Control Company, Houston TX) can be used to remove a substrate layer from additional underlying layers, if necessary, to avoid any longitudinal and lateral extension of the material. Once the substrate layer has been removed from the article proceed with die cutting the sample as described above.

If the substrate material is in the form of a wet wipe, open a new package of wet wipes and remove the entire stack from the package. Remove a single wipe from the middle of the stack, lay it out flat and allow it to dry completely prior to die cutting the sample for analysis.

A sample may be cut from any location containing the visually discernible zone to be analyzed. Within a zone, regions to be analyzed are ones associated with a three-dimensional feature defining a microzone. The microzone comprises a least two visually discernible regions. A zone, three-dimensional feature, or microzone may be visually discernable due to changes in texture, elevation, or thickness. Regions within different samples taken from the same substrate material may be analyzed and compared to each other. Care should be taken to avoid folds, wrinkles or tears when selecting a location for sampling.

Image Acquisition:

Set up and calibrate the micro-CT instrument according to the manufacturer's specifications. Place the sample into the appropriate holder, between two rings of low density material, which have an inner diameter of 25 mm. This will allow the central portion of the sample to lay horizontal and be scanned without having any other materials directly adjacent to its upper and lower surfaces. Measurements should be taken in this region. The 3D image field of view is approximately 35 mm on each side in the xy-plane with a resolution of approximately 5000 by 5000 pixels, and with a sufficient number of 7 micron thick slices collected to fully include the z-direction of the sample. The reconstructed 3D image resolution contains isotropic voxels of 7 microns. Images are acquired with the source at 45 kVp and 133 μA with no additional low energy filter. These current and voltage settings may be optimized to produce the maximum contrast in the projection data with sufficient x-ray penetration through the sample, but once optimized held constant for all substantially similar samples. A total of 1500 projections images are obtained with an integration time of 1000 ms and 3 averages. The projection images are reconstructed into the 3D image, and saved in 16-bit RAW format to preserve the full detector output signal for analysis.

Image Processing:

Load the 3D image into the image analysis software. Threshold the 3D image at a value which separates, and removes, the background signal due to air, but maintains the signal from the sample fibers within the substrate.

Three 2D intensive property images are generated from the threshold 3D image. The first is the Basis Weight Image. To generate this image, the value for each voxel in an xy-plane slice is summed with all of its corresponding voxel values in the other z-direction slices containing signal from the sample. This creates a 2D image where each pixel now has a value equal to the cumulative signal through the entire sample.

In order to convert the raw data values in the Basis Weight Image into real values a basis weight calibration curve is generated. Obtain a substrate that is of substantially similar composition as the sample being analyzed and has a uniform basis weight. Follow the procedures described above to obtain at least ten replicate samples of the calibration curve substrate. Accurately measure the basis weight, by taking the mass to the nearest 0.0001 g and dividing by the sample area and converting to grams per square meter (gsm), of each of the single layer calibration samples and calculate the average to the nearest 0.01 gsm. Following the procedures described above, acquire a micro-CT image of a single layer of the calibration sample substrate. Following the procedure described above process the micro-CT image, and generate a Basis Weight Image containing raw data values. The real basis weight value for this sample is the average basis weight value measured on the calibration samples. Next, stack two layers of the calibration substrate samples on top of each other, and acquire a micro-CT image of the two layers of calibration substrate. Generate a basis weight raw data image of both layers together, whose real basis weight value is equal to twice the average basis weight value measured on the calibration samples. Repeat this procedure of stacking single layers of the calibration substrate, acquiring a micro-CT image of all of the layers, generating a raw data basis weight image of all of the layers, the real basis weight value of which is equal to the number of layers times the average basis weight value measured on the calibration samples. A total of at least four different basis weight calibration images are obtained. The basis weight values of the calibration samples must include values above and below the basis weight values of the original sample being analyzed to ensure an accurate calibration. The calibration curve is generated by performing a linear regression on the raw data versus the real basis weight values for the four calibration samples. This linear regression must have an R2 value of at least 0.95, if not repeat the entire calibration procedure. This calibration curve is now used to convert the raw data values into real basis weights.

The second intensive property 2D image is the Thickness Image. To generate this image the upper and lower surfaces of the sample are identified, and the distance between these surfaces is calculated giving the sample thickness. The upper surface of the sample is identified by starting at the uppermost z-direction slice and evaluating each slice going through the sample to locate the z-direction voxel for all pixel positions in the xy-plane where sample signal was first detected. The same procedure is followed for identifying the lower surface of the sample, except the z-direction voxels located are all the positions in the xy-plane where sample signal was last detected. Once the upper and lower surfaces have been identified they are smoothed with a 15×15 median filter to remove signal from stray fibers. The 2D Thickness Image is then generated by counting the number of voxels that exist between the upper and lower surfaces for each of the pixel positions in the xy-plane. This raw thickness value is then converted to actual distance, in microns, by multiplying the voxel count by the 7 μm slice thickness resolution.

The third intensive property 2D image is the Volumetric Density Image. To generate this image divide each xy-plane pixel value in the Basis Weight Image, in units of gsm, by the corresponding pixel in the Thickness Image, in units of microns. The units of the Volumetric Density Image are grams per cubic centimeter (g/cc).

Micro-CT Basis Weight, Thickness and Volumetric Density Intensive Properties:

Begin by identifying the region to be analyzed. A region to be analyzed is one associated with a three-dimensional feature defining a microzone. The microzone comprises a least two visually discernible regions. A zone, three-dimensional feature, or microzone may be visually discernable due to changes in texture, elevation, or thickness. Next, identify the boundary of the region to be analyzed. The boundary of a region is identified by visual discernment of differences in intensive properties when compared to other regions within the sample. For example, a region boundary can be identified based by visually discerning a thickness difference when compared to another region in the sample. Any of the intensive properties can be used to discern region boundaries on either the physical sample itself or any of the micro-CT intensive property images. Once the boundary of the region has been identified, draw an oval or circular "region of interest" (ROI) within the interior of the region. The ROI should have an area of at least 0.1 mm2, and be selected to measure an area with intensive property values representative of the identified region. From each of the three intensive property images calculate the average basis weight, thickness and volumetric density within the ROI. Record these values as the region's basis weight to the nearest 0.01 gsm, thickness to the nearest 0.1 micron and volumetric density to the nearest 0.0001 g/cc.

EXAMPLES/COMBINATIONS

A. A spunbond nonwoven web for an absorbent article, the spunbond nonwoven web comprising:
   a first surface;
   a second surface; and
   a visually discernible pattern of three-dimensional features on the first surface or the second surface, wherein the three-dimensional features comprise one or more first regions and a plurality of second regions;

wherein the one or more first regions have a first value of an average intensive property, wherein the plurality second regions have a second value of the average intensive property, wherein the first value and the second value are different, and wherein the first value and the second value are greater than zero;

wherein the spunbond nonwoven web has a Single Layer Chroma value in the range of about 1.0 to about 3.5, according to the Delta Chroma and Single Layer Chroma Test; and wherein the spunbond nonwoven web has a Delta Chroma value in the range of about +0.1 to about +3.5, according to the Delta Chroma and Single Layer Chroma Test.

B. A nonwoven web for an absorbent article, the nonwoven web comprising:

a first surface;

a second surface; and a plurality of three-dimensional features extending from the first surface or the second surface;

wherein the nonwoven web has a Single Layer Chroma value in the range of about 1.0 to about 3.5, according to the Delta Chroma and Single Layer Chroma Test; and wherein the nonwoven web has a Delta Chroma value in the range of about +0.5 to about +3.5, according to the Delta Chroma and Single Layer Chroma Test.

C. A nonwoven web for an absorbent article, the nonwoven web comprising:

a first surface;

a second surface; and a plurality of three-dimensional features extending from the first surface or the second surface;

wherein the nonwoven web has a Single Layer Chroma value in the range of about 1.0 to about 3.5, according to the Delta Chroma and Single Layer Chroma Test;

wherein the nonwoven web has a Delta Chroma value in the range of about +0.5 to about +3.5, according to the Delta Chroma and Single Layer Chroma Test; and wherein a portion of the nonwoven web has a TS7 value in the range of about 1 dB $V^2$ rms to about 4.5 dB $V^2$ rms, according to the Emtec Test, and wherein the portion of the nonwoven web has a TS750 value in the range of about 6 dB $V^2$ rms to about 30 dB $V^2$ rms, according to the Emtec Test.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this present disclosure.

What is claimed is:

1. A nonwoven web for an absorbent article, the nonwoven web having one or more layers and comprising:

a first surface;

a second surface; and a visually discernible pattern of three-dimensional features on the first surface or the second surface, wherein the three-dimensional features comprise one or more first regions and a plurality of second regions;

wherein the one or more first regions have a first value of an average intensive property, wherein the plurality second regions have a second value of the average intensive property, wherein the first value and the second value are different, wherein the first value and the second value are greater than zero, and wherein the average intensive property is basis weight, volumetric density, or caliper;

wherein a non-white colorant is included in a composition used to create fibers of the non-woven web such that the non-woven web appears white to a human eye, wherein the composition includes 0.15% to 0.4% by weight of the non-white colorant;

wherein the nonwoven web has a Single Layer Chroma value in the range of about 1.0 to about 3.5, according to the Delta Chroma and Single Layer Chroma Test; and wherein the nonwoven web has a Delta Chroma value in the range of about +0.1 to about +3.5, according to the Delta Chroma and Single Layer Chroma Test.

2. The nonwoven web for an absorbent article of claim 1, wherein the nonwoven web has a Single Layer Chroma value in the range of about 1.5 to about 3.5, according to the Delta Chroma and Single Layer Chroma Test, and wherein the nonwoven web has a Delta Chroma value in the range of about +0.5 to about +3.5, according to the Delta Chroma and Single Layer Chroma Test.

3. The nonwoven web for an absorbent article of claim 1, wherein the nonwoven web has a Single Layer Chroma value in the range of about 1.5 to about 3.5, according to the Delta Chroma and Single Layer Chroma Test, and wherein the nonwoven web has a Delta Chroma value in the range of about +1.0 to about +3.5, according to the Delta Chroma and Single Layer Chroma Test.

4. The nonwoven web for an absorbent article of claim 1, wherein the nonwoven web has a Single Layer Chroma value in the range of about 1.5 to about 3.5, according to the Delta Chroma and Single Layer Chroma Test, and wherein the nonwoven web has a Delta Chroma value in the range of about +1.5 to about +3.5, according to the Delta Chroma and Single Layer Chroma Test.

5. The nonwoven web for an absorbent article of claim 1, wherein the non-white colorant comprises a blue colorant.

6. The nonwoven web for an absorbent article of claim 1, wherein the first average intensive property and the second average intensive property are basis weight.

7. The nonwoven web for an absorbent article of claim 1, wherein the first average intensive property and the second average intensive property are caliper.

8. The nonwoven web for an absorbent article of claim 1, wherein the first average intensive property and the second average intensive property are volumetric density.

9. The nonwoven web for an absorbent article of claim 1, wherein the nonwoven web comprises bonds at fiber intersections formed by passing hot air through the nonwoven web.

10. The nonwoven web for an absorbent article of claim 1, wherein the nonwoven web comprises calendar bonds configured to join the fibers together.

11. The nonwoven web for an absorbent article of claim 1, wherein the nonwoven web comprises a second, visually discernible pattern of three-dimensional features on the first surface or the second surface, wherein the three-dimensional features comprise one or more third regions and a plurality of fourth regions, and wherein the one or more third regions are different than the plurality of fourth regions in a value of an average intensive property.

12. The nonwoven web for an absorbent article of claim 1, wherein the nonwoven web comprises multicomponent fibers, and wherein at least one component of the multicomponent fibers is bio-based.

13. The nonwoven web for an absorbent article of claim 1, wherein the nonwoven web has a basis weight in the range of about 10 gsm to about 100 gsm according to the Basis Weight Test, and wherein the nonwoven web is a spunbond nonwoven web.

14. The nonwoven web for an absorbent article of claim 1, wherein a portion of the nonwoven web has a TS7 value in the range of about 1 dB $V^2$ rms to about 4.5 dB $V^2$ rms, according to the Emtec Test, and wherein the portion of the nonwoven web has a TS750 value in the range of about 6 dB $V^2$ rms to about 30 dB $V^2$ rms, according to the Emtec Test.

15. The nonwoven web for an absorbent article of claim 14, wherein the portion of the nonwoven web has a D value in the range of about 2 mm/N to about 6 mm/N, according to the Emtec Test.

16. An absorbent article comprising the nonwoven web of claim 1.

17. A nonwoven web for an absorbent article, the nonwoven web having one or more layers and comprising:
a first surface;
a second surface;
a plurality of continuous spunbond fibers; and
a visually discernible pattern of three-dimensional features on the first surface or the second surface, wherein the three-dimensional features comprise one or more first regions and a plurality of second regions;
wherein the one or more first regions have a first value of an average intensive property, wherein the plurality of second regions have a second value of the average intensive property, wherein the first value and the second value are different, wherein the first value and the second value are greater than zero, and wherein the average intensive property is basis weight, volumetric density, or caliper;
wherein a non-white colorant is included in a composition used to create fibers of the non-woven web such that the non-woven web appears white to a human eye, wherein the composition includes 0.15% to 0.4% by weight of the non-white colorant;
wherein the nonwoven web has a Single Layer Chroma value in the range of about 1.0 to about 3.5, according to the Delta Chroma and Single Layer Chroma Test; and
wherein the nonwoven web has a Delta Chroma value in the range of about +0.1 to about +3.5, according to the Delta Chroma and Single Layer Chroma Test.

18. The nonwoven web for an absorbent article of claim 17, wherein the nonwoven web has a Single Layer Chroma value in the range of about 1.5 to about 3.5, according to the Delta Chroma and Single Layer Chroma Test, and wherein the nonwoven web has a Delta Chroma value in the range of about +0.5 to about +3.5, according to the Delta Chroma and Single Layer Chroma Test.

19. A nonwoven web for an absorbent article, the nonwoven web having one or more layers and comprising:
a first surface;
a second surface; and
a first visually discernible pattern of three-dimensional features on the first surface or the second surface, wherein the three-dimensional features comprise one or more first regions and a plurality of second regions;
wherein the one or more first regions are different than the plurality of second regions in a value of a first average intensive property, wherein the first average intensive property is basis weight, volumetric density, or caliper;
wherein a non-white colorant is included in a composition used to create fibers of the non-woven web such that the non-woven web appears white to a human eye, wherein the composition includes 0.15% to 0.4% by weight of the non-white colorant;
wherein a first portion of the nonwoven web in the first visually discernible pattern has a Single Layer Chroma value in the range of about 1.0 to about 3.5, according to the Delta Chroma and Single Layer Chroma Test; and
wherein the first portion of the nonwoven web in the first visually discernible pattern has a Delta Chroma value in the range of about +0.1 to about +3.5, according to the Delta Chroma and Single Layer Chroma Test; and
a second visually discernible pattern of three-dimensional features on the first surface or the second surface, wherein the three-dimensional features comprise one or more third regions and a plurality of fourth regions, and wherein the one or more third regions are different than the plurality of fourth regions in a value of a second average intensive property.

20. The nonwoven web for an absorbent article of claim 19, wherein the first portion of the nonwoven web in the first visually discernible pattern has a Single Layer Chroma value in the range of about 1.5 to about 3.5, according to the Delta Chroma and Single Layer Chroma Test, and wherein the first portion of the nonwoven web in the first visually discernible pattern has a Delta Chroma value in the range of about +0.5 to about +3.5, according to the Delta Chroma and Single Layer Chroma Test.

21. The nonwoven web for an absorbent article of claim 20, wherein a second portion of the nonwoven web in the second visually discernible pattern has a Single Layer Chroma in the range of about 1.0 to about 3.5, according to the Delta Chroma and Single Layer Chroma Test, and wherein the second portion of the nonwoven web in the second visually discernible pattern has a Delta Chroma in the range of about +0.1 to about +3.5, according to the Delta Chroma and Single Layer Chroma Test.

22. The nonwoven web for an absorbent article of claim 19, wherein the first average intensive property and the second average intensive property are basis weight, caliper, or volumetric density.

* * * * *